(12) United States Patent
Demirci et al.

(10) Patent No.: US 12,702,979 B2
(45) Date of Patent: Aug. 11, 2026

(54) ISOLATION OF DIFFERENT EXTRACELLULAR VESICLE (EV) SUBPOPULATIONS

(71) Applicant: The Board of Trustees of the Leland Stanford Junior University, Stanford, CA (US)

(72) Inventors: Utkan Demirci, Stanford, CA (US); Mehmet Ozgun Ozen, Palo Alto, CA (US); Naside Gozde Durmus, Stanford, CA (US); Rakhi Gupta, Cupertino, CA (US); Sharon Pitteri, Palo Alto, CA (US); Fernando Jose Garcia Marques, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 883 days.

(21) Appl. No.: 17/504,947

(22) Filed: Oct. 19, 2021

(65) Prior Publication Data

US 2022/0118452 A1 Apr. 21, 2022

Related U.S. Application Data

(60) Provisional application No. 63/094,052, filed on Oct. 20, 2020.

(51) Int. Cl.

| | |
|---|---|
| ***B01L 3/00*** | (2006.01) |
| ***A61K 35/13*** | (2015.01) |

(Continued)

(52) U.S. Cl.

CPC ........ *B01L 3/502753* (2013.01); *A61K 35/13* (2013.01); *B01L 3/502761* (2013.01);

(Continued)

(58) Field of Classification Search

CPC ......... B01L 3/502753; B01L 3/502761; B01L 2300/0681; B01L 2300/0819;

(Continued)

(56) References Cited

U.S. PATENT DOCUMENTS

| | | | |
|---|---|---|---|
| 7,942,568 | B1 | 5/2011 | Branch et al. |
| 2017/0248508 | A1 | 8/2017 | Ward et al. |

(Continued)

OTHER PUBLICATIONS

Heinemann et al.,Benchtop isolation and characterization of functional exosomes by sequential filtration, Journal of Chromatography A, vol. 1372, (2014), pp. 125-135.*

(Continued)

*Primary Examiner* — Jennifer M.H. Tichy
(74) *Attorney, Agent, or Firm* — Quarles & Brady LLP

(57) ABSTRACT

An extracellular vesicle-containing sample can be processed using a device for isolating one or more subpopulations of the extracellular vesicles. The extracellular vesicle-containing sample is flowed through a flow chamber of the device under an applied fluid pressure, in which the device has one or more inlets and two or more outlets in fluid communication with one another via the flow chamber. The device has one or more filters in the flow chamber between the inlet(s) and at least one of the outlet(s). The extracellular vesicle-containing sample is flowed through the filter(s) in the flow chamber to sort the extracellular vesicles of extracellular vesicle-containing sample by size into two or more subpopulations of the extracellular vesicles. At least one of the subpopulations that has been sorted flows out of a corresponding one of the outlets. Surface marker-based exosome sorting using magnetic beads may be used after the size-based exosome isolation.

16 Claims, 32 Drawing Sheets

(51) Int. Cl.
*B03C 1/01* (2006.01)
*B03C 1/28* (2006.01)

(52) U.S. Cl.
CPC ................ *B03C 1/01* (2013.01); *B03C 1/288* (2013.01); *B01L 2300/0681* (2013.01); *B01L 2300/0819* (2013.01); *B01L 2300/0864* (2013.01); *B01L 2300/0877* (2013.01); *B01L 2300/0896* (2013.01); *B01L 2400/043* (2013.01); *B01L 2400/0436* (2013.01); *B01L 2400/0487* (2013.01); *B03C 2201/18* (2013.01); *B03C 2201/26* (2013.01)

(58) Field of Classification Search
CPC ..... B01L 2300/0864; B01L 2300/0877; B01L 2300/0896; B01L 2400/043; B01L 2400/0436; B01L 2400/0487; A61K 35/13; B01C 1/01; B01C 1/288; B01C 2201/18; B01C 2201/26
USPC .......................................................... 435/375
See application file for complete search history.

(56) References Cited

U.S. PATENT DOCUMENTS

| | | | |
|---|---|---|---|
| 2018/0161775 | A1 | 6/2018 | Kapur et al. |
| 2018/0280977 | A1 | 10/2018 | Baday et al. |
| 2019/0049438 | A1 | 2/2019 | Liu et al. |
| 2020/0129981 | A1 | 4/2020 | Mao et al. |

OTHER PUBLICATIONS

Liu et al., The Exosome Total Isolation Chip, ACS Nano, 2017, 11(11):10712-10723.

Thery et al., Isolation and Characterization of Exosomes from Cell Culture Supernatants and Biological Fluids, Current Protocols in Cell Biology, 2006, Supplement 30, pp. 3.22.1-3.22.29.

PCT International Search Report and Written Opinion, PCT/US2021/055539, Jan. 27, 2022, 14 pages.

European Patent Office, Extended European Search Report for application No. 21883668.2, Sep. 10, 2024, 9 pages.

* cited by examiner

Tissue Exosomes

Exosome Origin

Mean Size (nm)

200
150
100
50
0

***

Plasma
Tissue

Exosome Concentration (particle/mL)

$5\times10^{12}$
$4\times10^{12}$
$3\times10^{12}$
$2\times10^{12}$
$1\times10^{12}$
0

****

Plasma
Tissue

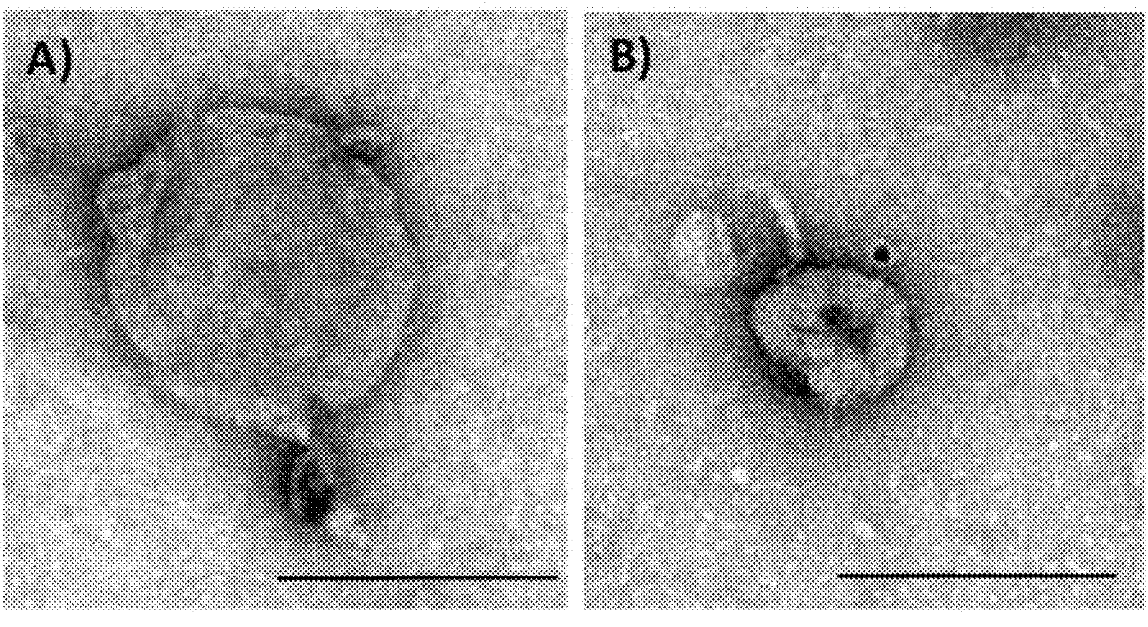
FIG. 17A
FIG. 17B
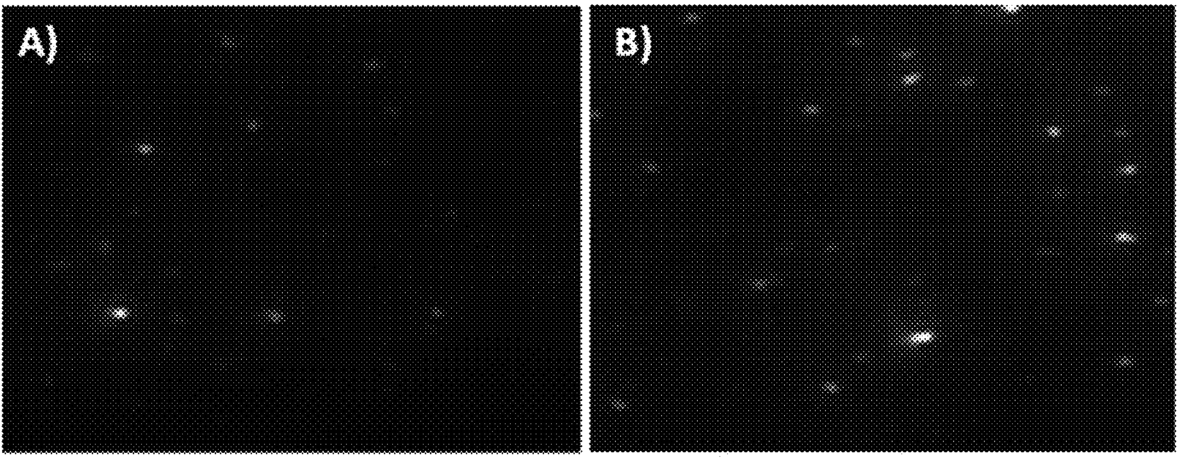
FIG. 18A
FIG. 18B

Exosomes

Microvesicles

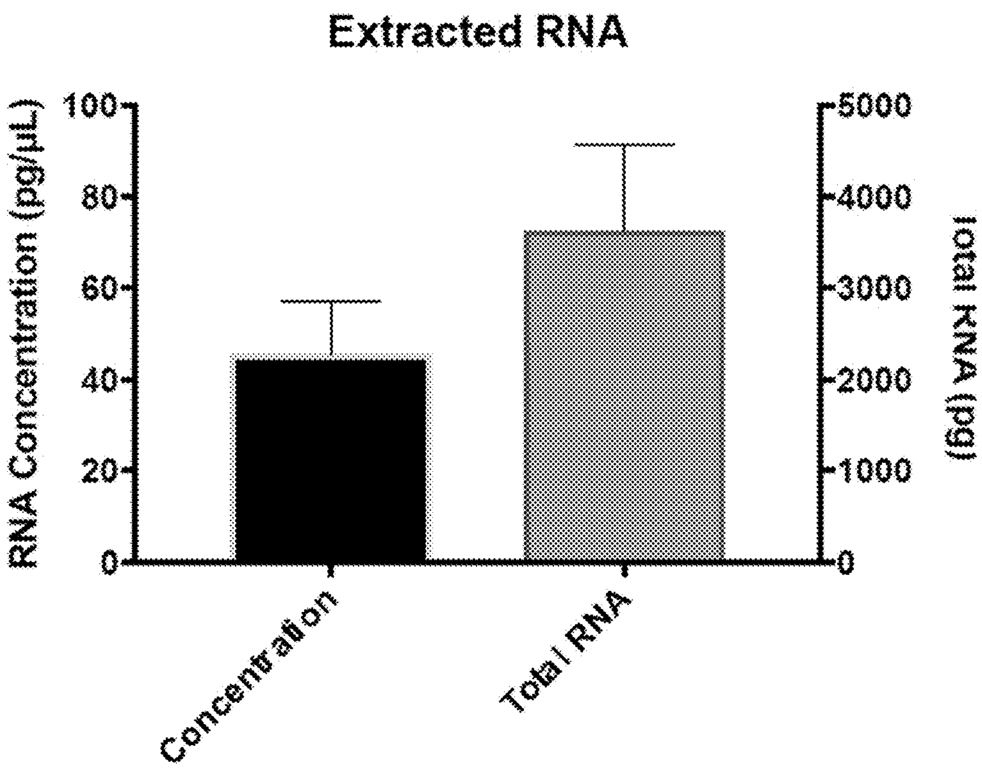
FIG. 26C
Exo-RNA Concentration
Exo-RNA (ng/µL)
2.0
1.5
1.0
0.5
0.0
*
Plasma - 500µL
Plasma - 100µL
FIG. 27A
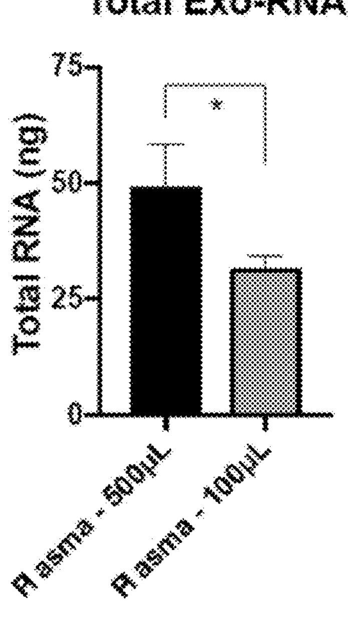
FIG. 27B

ISOLATION OF DIFFERENT EXTRACELLULAR VESICLE (EV) SUBPOPULATIONS

CROSS-REFERENCE TO RELATED APPLICATION

This application claims the benefit of U.S. Provisional Patent Application No. 63/094,052 entitled "Isolation of Different Extracellular Vesicle (EV) Subpopulations" filed Oct. 20, 2020, the contents of which are incorporated by reference herein in its entirety for all purposes.

STATEMENT OF FEDERALLY SPONSORED RESEARCH OR DEVELOPMENT

This invention was made with Government support under contracts AI120683, CA199075, and GM108584 awarded by the National Institutes of Health. The Government has certain rights in the invention.

TECHNICAL FIELD

This disclosure relates to the isolation of extracellular vesicle subpopulations using the Exosome Total Isolation Chip (ExoTIC) platform.

BACKGROUND

Extracellular vesicles ("EVs") are secreted from cells through various mechanisms and they can range from 10 nm to 1 micrometers in size. Exosomes are a subset of extracellular vesicles and are tiny extracellular vesicles (<120 nm). Extracellular vesicles carry critical genomic and proteomic information, and enable various applications in cell-to-cell communication, reprogramming, metastasis, disease detection, therapeutics, and prognostics. Various approaches and tools have been developed for isolating EVs and performing downstream molecular analysis, when large quantities of sample volumes are available (>1 mL). However, isolating EVs from small tissue nodules (<1 mm in diameter) and small samples volumes (<100 μl) presents a formidable challenge, as processing small sample volumes is challenging and bio-banked human samples are often only available in limited quantities.

SUMMARY

As noted above, exosomes are small lipid bilayer extracellular vesicles (30-120 nm in diameter) secreted by most cell types including cancer cells, which are present in body fluids, such as plasma, serum, saliva, urine, and lavage. EVs and exosomes play pivotal roles in cell-to-cell communication and signaling broadening their applications across multiple fields. They are intercellular transport vesicles and signaling parcels that carry and transfer donor cell cargoes (i.e., mRNAs, microRNAs, long noncoding RNAs, mitochondrial DNAs, single-stranded DNAs, double-stranded DNAs, proteins, and lipids) into recipient cells and tissues to execute biological or pathological functions. EV mediated cargo contains "information-coded" messages that have many important physiological and pathological implications. For instance, cancer cell-derived exosomes can spread cancer-specific microRNAs to other cells to promote cancer metastasis. It has been shown that exosomes circulating in blood and other body fluids of cancer patients contain specific signatures or biomarkers that reflect the disease state and progression of the originating cancer cells. Thus, profiling of EV-derived and exosome-derived biomarkers might provide a promising avenue for early diagnoses and improved prognosis of various cancers, including lung, kidney, prostate, ovarian, breast, pancreatic cancer, and hematological malignancies.

According to one aspect, a method is disclosed of processing an extracellular vesicle-containing sample using a device for extracellular vesicle isolation and isolating one or more subpopulations of the extracellular vesicles. The extracellular vesicle-containing sample flows through a flow chamber of the device for extracellular vesicle isolation under an applied fluid pressure. The device has one or more inlets and at least two outlets which are placed in fluid communication with one another via the flow chamber and further has one or more filters in the flow chamber between at least one of the inlets and at least one of the at least two outlets. During the step of flowing, the extracellular vesicle-containing sample is flowed through the one or more filters in the flow chamber to sort the extracellular vesicles of extracellular vesicle-containing sample by size into two or more subpopulations of the extracellular vesicles. At least one of the subpopulations of the extracellular vesicles that have been sorted by size after passing through the one or more filters is then flowed out of a corresponding one of the outlets.

In some forms, after the step of flowing the extracellular vesicle-containing sample through the one or more filters in the flow chamber to sort the extracellular vesicles of extracellular vesicle-containing sample by size into two or more subpopulations of the extracellular vesicles, labeled magnetically-responsive particles may be introduced to at least one of the subpopulations of the extracellular vesicles that are configured to bind to at least some members of the subpopulations of the extracellular vesicles. Then, the subpopulation of the extracellular vesicles may be flowed through a channel having a magnetic field applied thereto to further separate members of the subpopulation that are bound to the labeled magnetically-responsive particles from members of the subpopulation that are not bound to the labeled magnetically-responsive particles. Those further separated members may be flowed from different outlets of the channel. In some forms, the method may further include, during introducing labeled magnetically-responsive particles to at least one of the subpopulations of the extracellular vesicles that are labeled to bind to at least some members of the subpopulations of the extracellular vesicles, acoustic mixing the magnetically-responsive particles with the respective subpopulation of the extracellular vesicles. In some forms, a combination of separation by mechanical filtration and binding to labeled magnetically-responsive particles of the respective subpopulations of the extracellular vesicles fractionalizes the extracellular vesicles by both size and surface markers.

In some forms, the one or more inlets may include different inlets including (i) at least one inlet for introducing the extracellular vesicle-containing sample to the flow chamber for flow through the one or more filters and (ii) at least one inlet for providing an evacuating flow to flow least one of the subpopulations of the extracellular vesicles from a portion of the flow chamber. At least one inlet for providing the evacuating flow may be positioned between two filters of the one or more filters in the flow chamber, such that the evacuating flow isolates the extracellular vesicles in the extracellular vesicle-containing sample having sizes between the two filter filtering sizes associated with the two filters and causes the extracellular vesicles that have been isolated to flow out a corresponding outlet of the at least two outlets.

In some forms, the outlets may include (i) at least one waste outlet for a portion of the extracellular vesicle-containing sample that has passed through all of the one or more filters and (ii) at least one filtered extracellular vesicle outlet out of which flows at least one of the subpopulations of the extracellular vesicles that have been sorted by size after passing through some, but not all, of the one or more filters.

In some forms, the inlets may include (i) at least one inlet for introducing the extracellular vesicle-containing sample to the flow chamber for flow through the one or more filters and (ii) at least one inlet for providing an evacuating flow to flow at least one of the subpopulations of the extracellular vesicles from a portion of the flow chamber; and the outlets may include (i) at least one waste outlet for a portion of the extracellular vesicle-containing sample that has passed through all of the one or more filters and (ii) at least one filtered extracellular vesicle outlet out of which flows at least one of the subpopulations of the extracellular vesicles that have been sorted by size after passing through some, but not all, of the one or more filters. The outlets may include three or more outlets including at least one waste outlet for a portion of the extracellular vesicle-containing sample that has passed through all of the one or more filters and at least two filtered extracellular vesicle outlets out of each of which flow a corresponding one of the subpopulations of the extracellular vesicles that have been sorted by size after passing through some, but not all, of the one or more filters. The two or more filtered extracellular vesicle outlets may sort the extracellular vesicle-containing sample into subpopulations of the extracellular vesicles having different and non-overlapping size ranges. Taken in series, a filtration size of the one or more filters in the flow chamber may progressively decrease between the inlet for introducing the extracellular vesicle-containing sample and the waste outlet for a portion of the extracellular vesicle-containing sample that has passed through all of the one or more filters. The filtration size of the one or more filters in the flow chamber may be filters between 200 nanometers and 30 nanometers in size (generally corresponding to the sizes of EVs).

In some forms, the extracellular vesicle-containing sample may include exosomes released from pancreatic tumor tissue.

In some forms, the extracellular vesicles in the extracellular vesicle-containing sample may be between 50-200 nanometers in size.

In some forms, prior to the step of flowing the extracellular vesicle-containing sample through a flow chamber of the device for extracellular vesicle isolation under an applied fluid pressure, the extracellular vesicle-containing sample may be pre-filtered to remove cells, bacterial contaminants, and other large cellular fragments.

In some forms, the extracellular vesicle-containing sample may be or may be derived from one of blood, plasma, urine, cerebral spinal fluid, semen, and breast milk.

According to another aspect, a system is disclosed for processing an extracellular vesicle-containing sample to isolate one or more subpopulations of the extracellular vesicles. The system includes a flow chamber defining a fluid pathway through the flow chamber extending from at least one inlet at which the extracellular vesicle-containing sample is introduced into the flow chamber, through a plurality of filters in the flow chamber in which the filters are of progressively decreasing filtration size along the fluid pathway so as to isolate a respective subpopulation of the extracellular vesicles between adjacent filters that has a size distribution defined by a filtration range between the adjacent filters, and to at least one waste outlet at which a portion of the extracellular vesicle-containing sample exits the flow chamber after having passed through all of the filters. The system further includes at least one evacuating flow inlet in fluid communication with the flow chamber. The evacuating flow inlet(s) are disposed between adjacent filters along the fluid pathway and provide an evacuating flow to flow the respective subpopulation of the extracellular vesicles between adjacent filters (that also has the size distribution defined by the filtration range between the adjacent filters from the flow chamber to at least one filtered extracellular vesicle outlet of the flow chamber).

In some forms, along the filtered exosome outlet(s) of the flow chamber a channel may be provided that first has an inlet that provides labeled magnetically-responsive particles to the corresponding subpopulations of the extracellular vesicles that are labeled to bind to at least some members of the corresponding subpopulation of the extracellular vesicles and then has a magnet positioned along the channel that further directs the corresponding subpopulation of the extracellular vesicles bound to the labeled magnetically-responsive particles and the corresponding subpopulation of the extracellular vesicles not bound to the labeled magnetically-responsive particles to respective ones of a pair of outlets at the end of the channel of the filtered extracellular vesicle outlet(s).

In some forms, the system may further include an acoustic mixer disposed along the channel of the filtered extracellular vesicle outlet(s) of the flow chamber in the vicinity of the inlet that provides labeled magnetically-responsive particles to the corresponding subpopulations of the extracellular vesicles.

In some forms, the evacuating flow inlet(s) may include at least two evacuating flow inlets each disposed between a respective pair of adjacent filters and having a respective filtered extracellular vesicle outlet. Each of the evacuating flow inlets provide a respective evacuating flow to flow the respective subpopulation of the extracellular vesicles between the respective adjacent filters that has the size distribution defined by the filtration range between the respective adjacent filters from the flow chamber to the respective filtered extracellular vesicle outlet of the flow chamber.

These and still other advantages of the invention will be apparent from the detailed description and drawings. What follows is merely a description of some preferred embodiments of the present invention. To assess the full scope of the invention, the claims should be looked to as these preferred embodiments are not intended to be the only embodiments within the scope of the claims.

BRIEF DESCRIPTION OF THE FIGURES

FIGS. 3*a* and 3*b* are size profiling of extracellular vesicles isolated from two cell lines; FIGS. 3*c* and 3*d* are size profiling of intracellular vesicles isolated from two cell lines; and FIGS. 3*e* and 3*f* are mode peak size and concentration, respectively, of extracellular vesicles and intracellular vesicles isolated/extracted from two cell lines.

FIG. 10 A provides a schematic illustration of the study design. A pre-clinical model of human PDAC was successfully established. Working with this model, mouse plasma samples and primary pancreatic cancer tissue samples were collected. Exosomes isolated from different pre-clinical sample types then were analyzed for size, morphology, and molecular content. Proteomic analysis was performed on exosome samples from the PDAC mouse model to identify human proteins. FIGS. 10B and 10C are schematic illustrations of the ExoTIC device in both assembled and exploded forms, respectively. The device comprises an inlet, multiple layers of poly (methyl methacrylate) (PMMA), a 50 nm nanoporous low-protein-binding filter, a paper pad, screws, nuts and an outlet. FIG. 10D shows schematically a process of exosome isolation on the ExoTIC nano-filter membrane. Intact exosomes (green) are enriched and purified at the filter, whereas the free proteins (orange) and nucleic acids (yellow) are washed away and collected as waste. Thus, isolated exosomes are concentrated in front of the membrane. Then, exosomes are washed by the introduction of PBS through the platform to minimize the contamination and to remove all the plasma components. The exosomes isolated and washed with our tool are then concentrated at a volume of ~400 μL in washing buffer. After washing and concentration steps, exosomes can be collected at the outlet with a simple micropipetting step.

FIG. 11A is a schematic illustration of the animal study design. The AsPC-1 human pancreatic carcinoma cell line was used to establish the orthotopic mouse model of pancreatic cancer. Orthotopic mice were sacrificed after 5, 6, and 7 weeks of implantation, respectively; and the primary pancreatic tumor were harvested. Harvested tissue was then digested and homogenized into a 5-10 mL tissue lysate. In addition, mouse plasma (100 μL) was collected after 5, 6, and 7 weeks of implantation, respectively. Each mouse plasma and tissue lysate sample was then processed for exosome isolation, physical characterization, and downstream proteomic analysis. FIG. 11B illustrates creating an orthotopic model of human PDAC in mice, using AsPC-1 human pancreatic carcinoma cells. FIG. 11C shows a representative ultrasound image of an orthotopic pancreatic tumor.

FIG. 12A shows the size and concentration (week 5-6, *=0.132; week 6-7, **=0.003; week 5-7, *=0.049) change of exosomes isolated from tissue samples and exosomal size distribution profile. FIG. 12B shows the size (week 5-7, *=0.0006; week 6-7, <0.0001) and concentration (week 5-7, =0.0021; week 6-7, *=0.036) change of exosomes isolated from plasma samples and exosomal size distribution profile. FIG. 12C shows the comparison of mean sizes (*=0.0005) and concentrations (<0.0001) of exosomes isolated from plasma and tissue samples. FIG. 12**D shows a representative TEM image of exosomes isolated from mouse pancreatic cancer tissues using a scale bar equal to 100 nm. Two-tailed t-test was performed to analyze the obtained data. Error bars in the graphs represent the standard error of the mean (SEM).

FIG. 13A is a Venn diagram of identified human proteins from exosomes isolated from mouse plasma (yellow, large circle), tissue (blue, medium circle), and secreted media from AsPC-1 pancreatic cancer cells (red, small circle) by LC-MS/MS. The identified human proteins from each source we subjected to gene enrichment by GO Biological process as illustrated in FIG. 13B (plasma, top; tissue, middle; ASPC-1, bottom), GO Cellular component as illustrated in FIG. 13C (plasma, top two groups; tissue, third group; ASPC-1, bottom group), molecular function p-values as indicated as * p-value<0.05, p-value<0.01, *p-value<0.001, and **p-value<0.0001 as illustrated in FIG. 13D (plasma, top; tissue, middle; ASPC-1, bottom), and transcription factor (TF) enrichment and network from the common identified proteins from all sources using FunRich 3.1.3 as illustrated in FIG. 13**E. The size of the (TF) indicates the p-value of the enrichment and the thickness of the edges represents the degree of confidence of the interaction according to STRING-db.

FIG. 14A illustrates iBAQ sorted heatmap of the top and bottom exosome identified-proteins quantification from plasma, tissue, and cell culture (from left to right). The quantification levels are expressed in Z-score units calculated as $\log_{10}$ normalized using the average of the quantification of every sample and standardized using the standard deviation. The color is depicted as indicated in the legend. FIG. 14B shows the dynamic range of LC-MS/MS analysis of the exosome proteins identified from three different sources (tissue, plasma and cell culture medium). Ranking of proteins according to the average of their absolute amounts. Quantification is based on added peptides intensities extracted from the MS1 of the proteins.

FIGS. 17A-B are representative TEM images of exosomes isolated from mouse pancreatic tumor tissues. FIG.

17A is a TEM image without immunogold labelling and FIG. 17B is a TEM image with immunogold labeling for CD63 (dark spots) (gold nanoparticle diameter=10 nm) (Scale bar=200 nm).

FIGS. 18A-B are nanoparticle tracking analysis (NTA) of exosomes isolated from mouse blood plasma (FIG. 18A) and mouse pancreatic tumor tissue (FIG. 18B).

FIG. 21A is a schematic illustration of the design and the components of ExoTIC platform assembled with 200 nm PES filter to isolate microvesicles. FIG. 21B is a schematic of the assembled ExoTIC chip.

FIG. 21C is an assembled ExoTIC devices processing culture media harvested from MSC cultures for MV isolation mounted on a syringe pump.

FIG. 22A are exosomes and FIG. 22B are microvesicles. Nanoparticle Tracking Analysis (NTA) of extracellular vesicles represented distinct size groups. Exosomes with a mean size of 119 nm. Microvesicles, a more heterogenous group with a mean size of 358 nm.

FIGS. 26A-C provide data pertaining to plasma derived EV isolation and the repeatability of the process. FIG. 26A provides size profiling of EVs isolated from aliquots of the same plasma sample (100 μL each, n=9). FIG. 26B shows peak size values (Mean and mode, nm) of the isolated EVs from the aliquots (n=9). FIG. 26C shows concentration of RNA and total RNA extracted from the EVs isolated from plasma aliquots (n=5).

FIGS. 27A-B show improved RNA yield from plasma-derived exosomes obtained from 500 μL and 100 μL of plasma samples. FIG. 27A shows Exosomal RNA concentration and FIG. 27B shows total Exosomal RNA.

DETAILED DESCRIPTION

Figure 1:
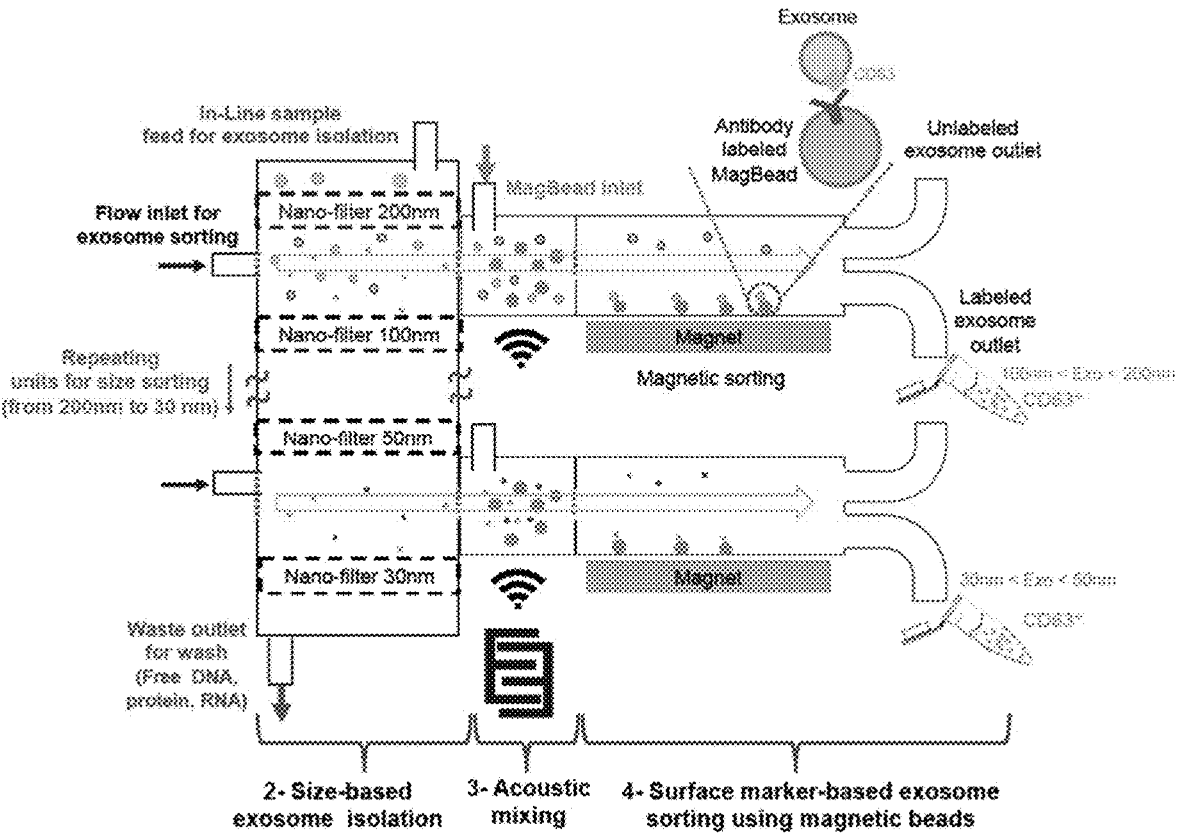
FIG. 1 illustrates a multimodal multiplexed EV profiling using multiplexed Multifunctional Exosome Sorter (MFES) platforms.

With reference being made to the following examples, automated instruments and parallel/series multiplexed processing using disposable isolation kits on the automated tool are disclosed. The disposable EV isolation device can be injection molded or by the aid of other high throughput manufacturing techniques. The disposable piece of the device can be integrated with larger automated sample handling and fluid processing equipment. After introducing a Multifunctional Exosome Sorter (MFES), various examples of isolation of sorting of subpopulations will be described.

EXAMPLES

Below are examples of specific embodiments for carrying out the present invention. The examples are offered for illustrative purposes only, and are not intended to limit the scope of the present invention in any way. It will be appreciated that while in many instances exosome isolation is described, that such isolation of exosomes is considered to be exemplary and that any EV may be isolated in the manners described.

Efforts have been made to ensure accuracy with respect to numbers used (e.g., amounts, temperatures, etc.), but some experimental error and deviation should, of course, be allowed for.

Example I: Multifunctional Exosome Sorter (MFES) and Auto-MFES

The biological effect of extracellular vesicles/exosomes is complex and reflects a heterogeneity in the exosome population being produced by a given cell type under specific conditions. Studies have shown that exosomes produced by cells can be separated by size and surface markers. Each exosome subset has unique biological properties and cargo composition. To date, no approach has been utilized to investigate whether exosome subsets have unique roles in initiating and perpetuating disease and/or health, largely due to the lack of a reliable experimental platform. However, a comprehensive assessment of the biological function and cargo characteristics of small and large size exosome subsets from healthy and diseased has been hindered by the lack of a reliable and reproducible method to separate exosome subsets from cell media compatible with available multi-omics methods for in-depth cargo analysis. To address this unmet need, we have designed the Multifunctional Exosome Sorter (MFES) that can dissect the whole exosome population into subpopulations based on size and surface markers. The size of the vesicles can be important as the size determines the origination mechanisms behind exosomes that also directly determine their content. For instance, larger microvesicles are formed by budding of the cellular membrane and have a part of the membrane surface markers and cytoplasm budding out with them similar to RNA virus budding mechanisms, e.g. HIV. Cargo such as DNA and mitochondria are reported to be associated with these vesicles. On the other hand, smaller vesicles are formed first inside the cell and then released out to the exterior similar to a cellular disposal mechanism. On the largest end of the spectrum, there are apoptotic vesicles that carry DNA that are released from dying cells. This heterogenous broad spectrum carries unknown signals using a novel technology to enable us uniquely sort subpopulations of exosomes namely focusing two fundamental fractionation mechanisms that distinguishes a vesicle's signature and cargo, i.e., (i) size, and (ii) surface markers.

Multifunctional Exosome Sorter (MFES) is a technological innovation merging multiple technologies, as there have been several approaches over the past decade to isolate exosomes from biological fluids. The previously developed ExoTIC platform could purify large amounts of exosomes via size-based sorting with high yield. See, for example, U.S. Patent Application Publication No. 2019/0049438 published on Feb. 14, 2019, which is incorporated by reference for all purposes as if set forth in its entirety herein. This platform provided major advantages over the common ultracentrifuge (UC) method for exosome purification. However, currently available technologies do not allow evaluation of the unique properties of EV and exosome subsets and how they influence cell biology and functional responses. Exosome cargo characterization has not been comprehensively performed due to the limited yields of traditional exosome purification methods and unpredictable quality of the cargo extractions. The newly disclosed technology overcomes these barriers by not only providing high yield/high quality exosome preparations from cell media, but also allows separation of exosomes into (i) large and small size populations by integrating size-based exosome isolation with (ii) multiplex and multimodal sorting of exosomes for surface markers via multiple magnetically collectible immune-capture beads as illustrated in FIG. 1. Some of the advantages of this approach over all other existing commercial methods is that it can provide up to 1000-fold higher yield compared to the common ultracentrifuge method, thus requiring much less volume, hence, significantly increasing efficiency and reducing cost. The higher yield and purity exosome subsets can allow unprecedented exosome analysis to be conducted to identify rare molecular signatures that are routinely lost with traditional methods.

Figure 2:
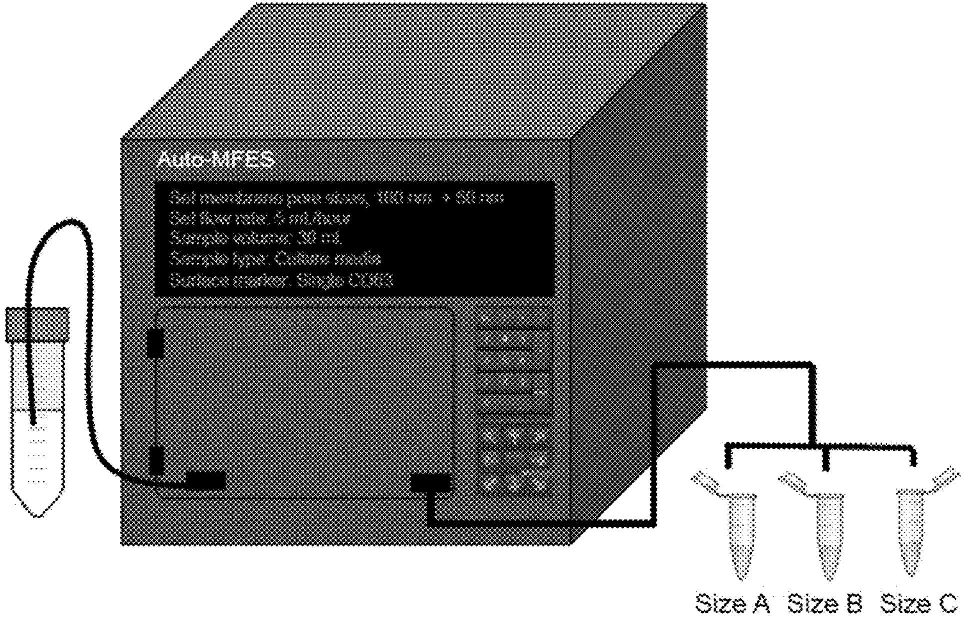
FIG. 2 is an automatic MFES device design to isolate different exosomal subpopulations.
Figure 3A:
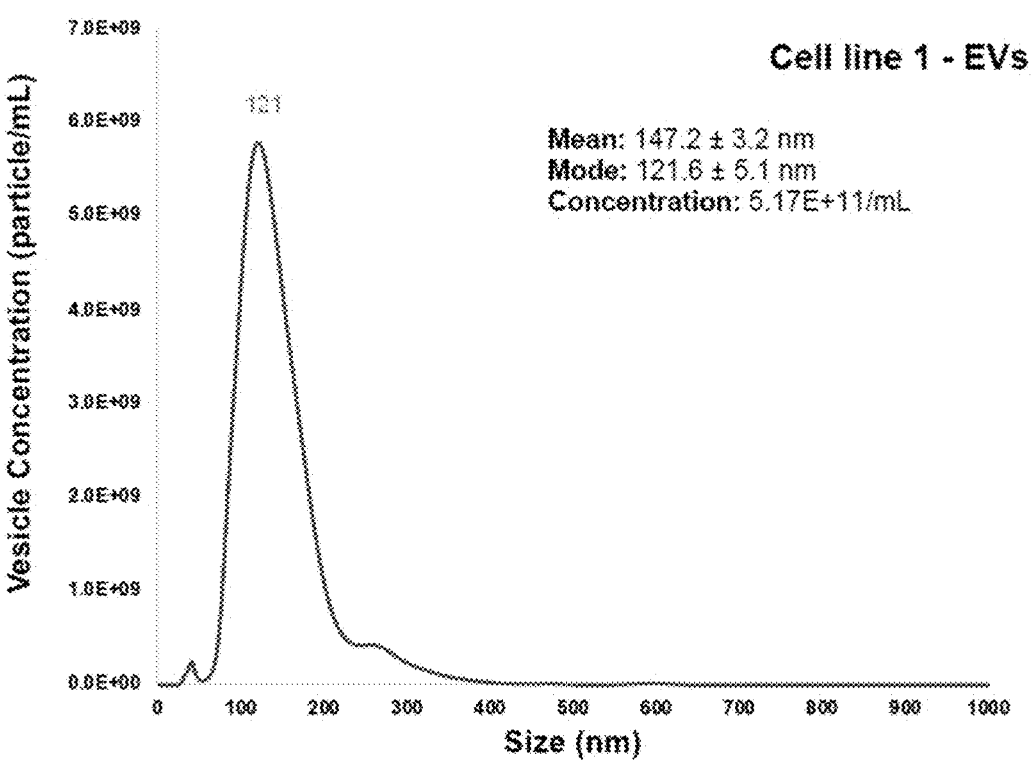
FIGS. 3*a*-3*e* illustrate quantification of EV (extracellular vesicles) and InVe (intracellular vesicles) isolated from two cell lines.
Figure 3B:
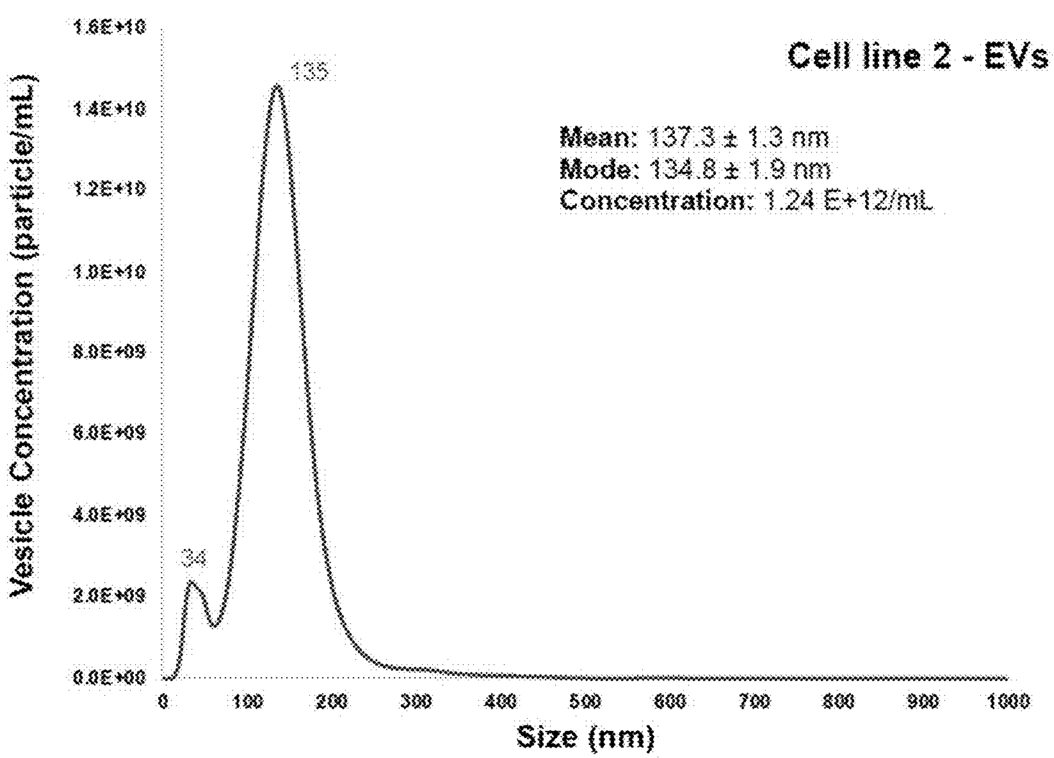
Figure 3C:
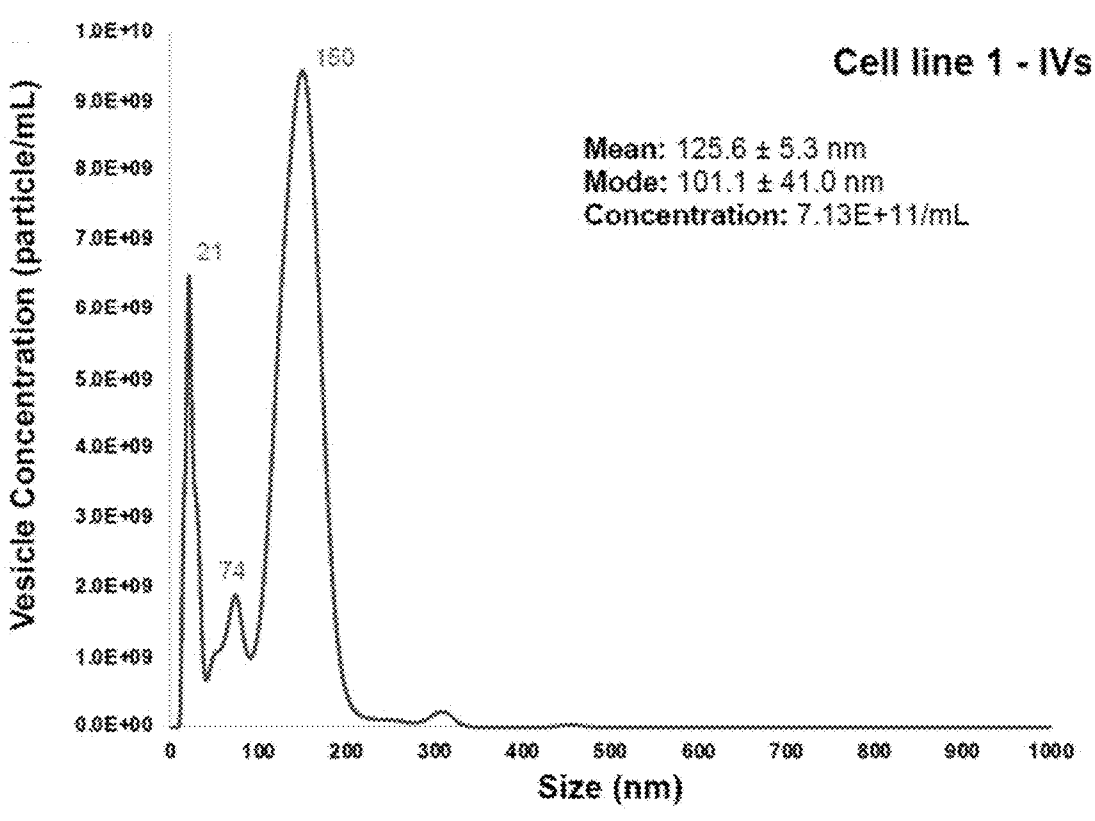
Figure 3D:
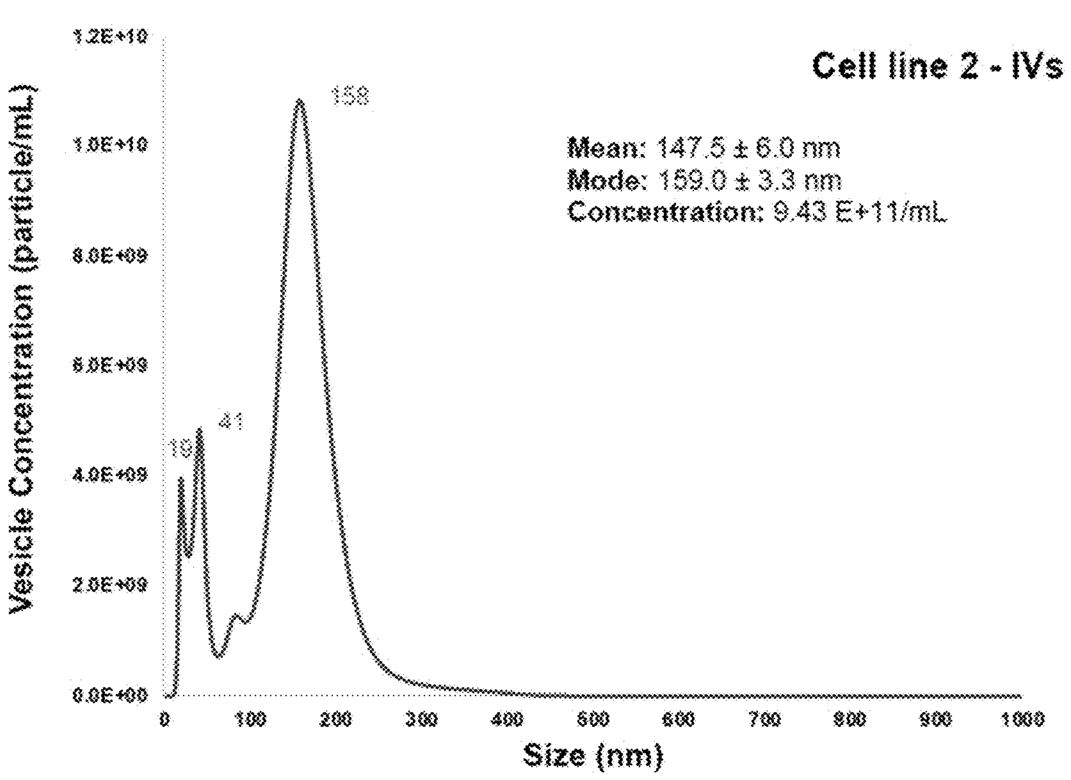
Figure 3E:
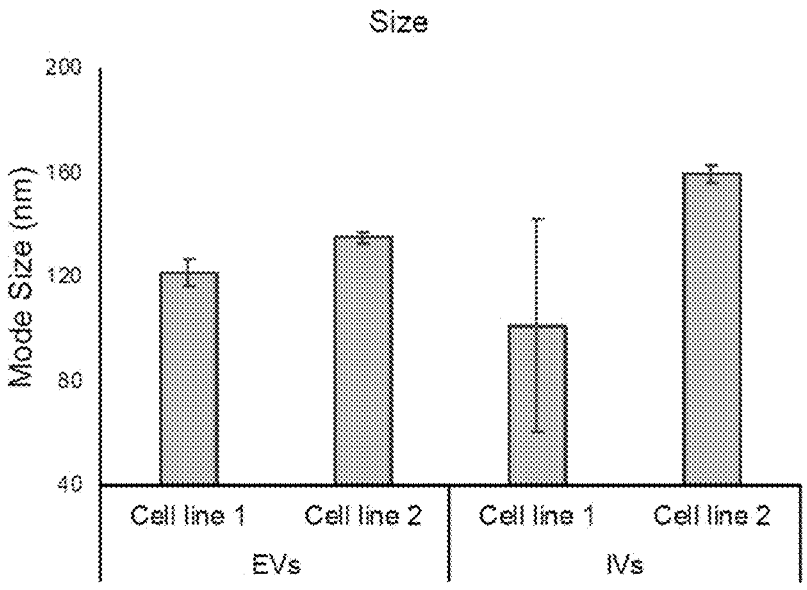
Figure 3F:
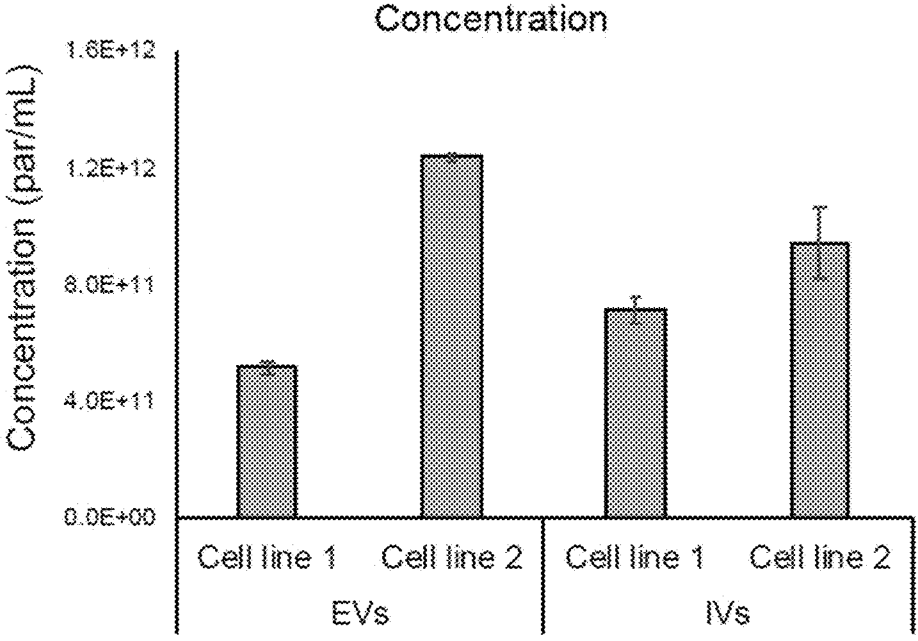
Figure 4:
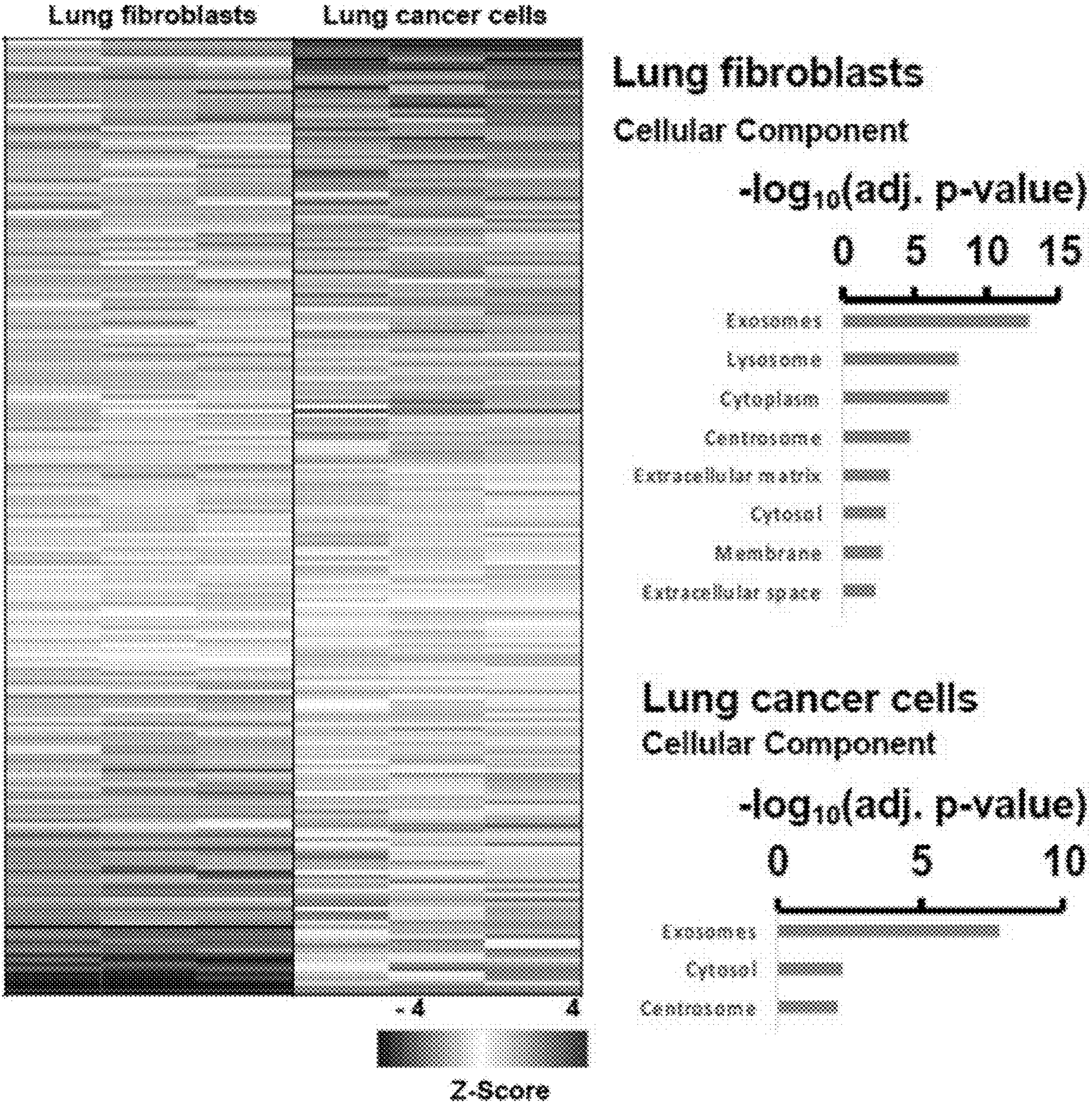
FIG. 4 illustrates proteomic comparison of exosomes isolated from monocultures of lung fibroblasts and lung cancer cells.
Figure 5:
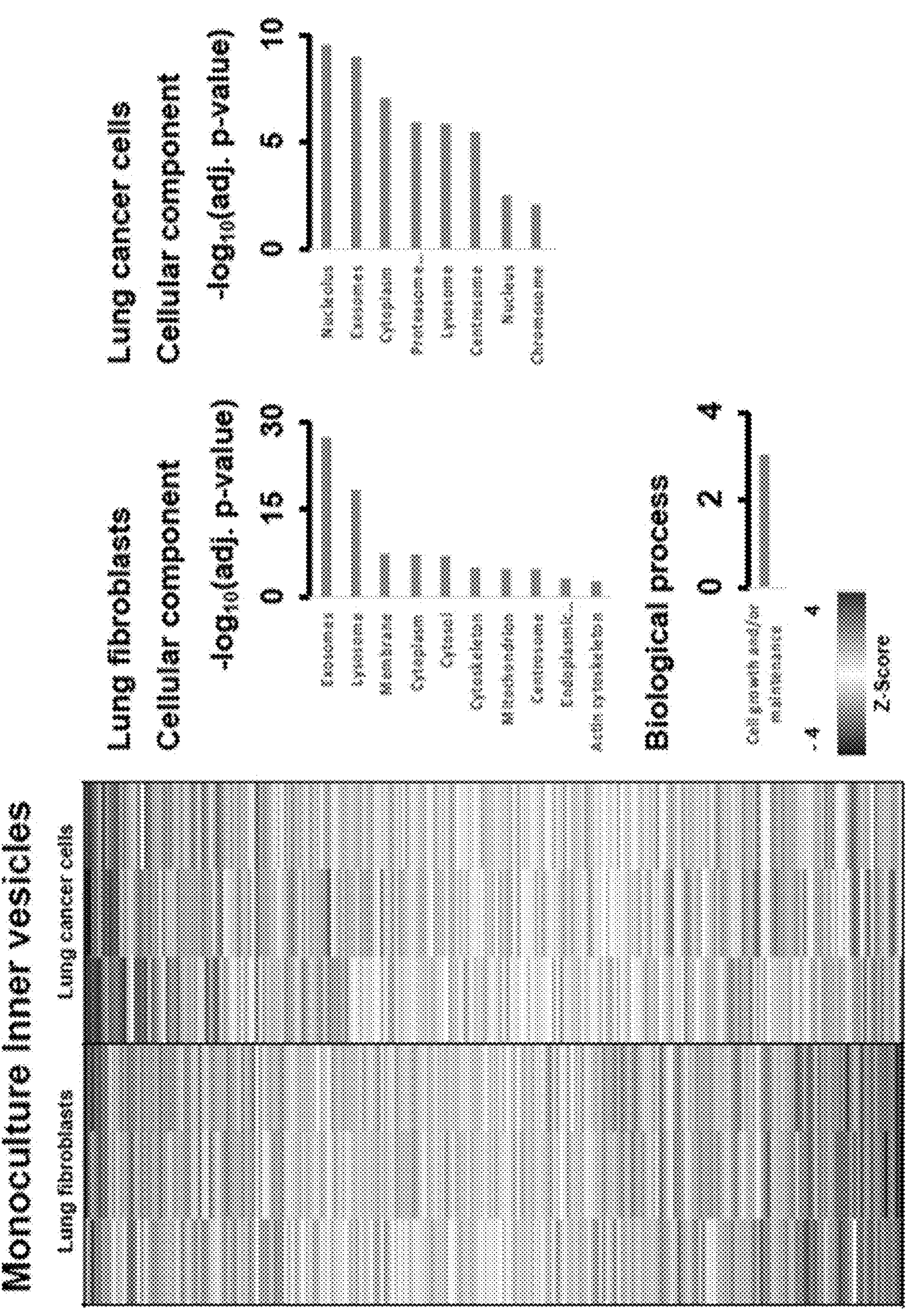
FIG. 5 illustrates proteomic comparison of intracellular vesicles isolated from monocultures of lung fibroblasts and lung cancer cells.
Figure 6:
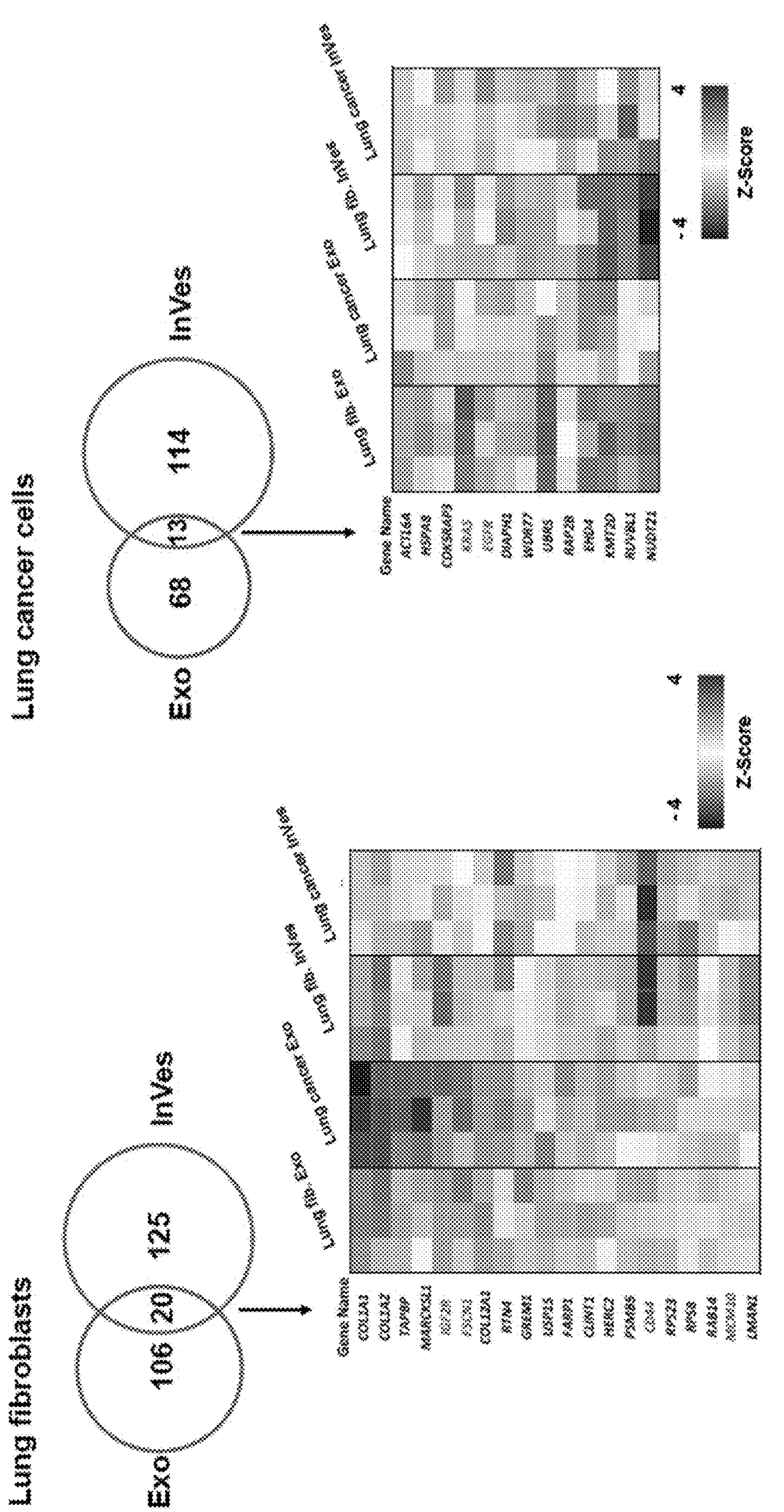
FIG. 6 illustrates proteomic comparison of exosomes and intracellular vesicles isolated from monocultures of lung fibroblasts and lung cancer cells.
Figure 7:
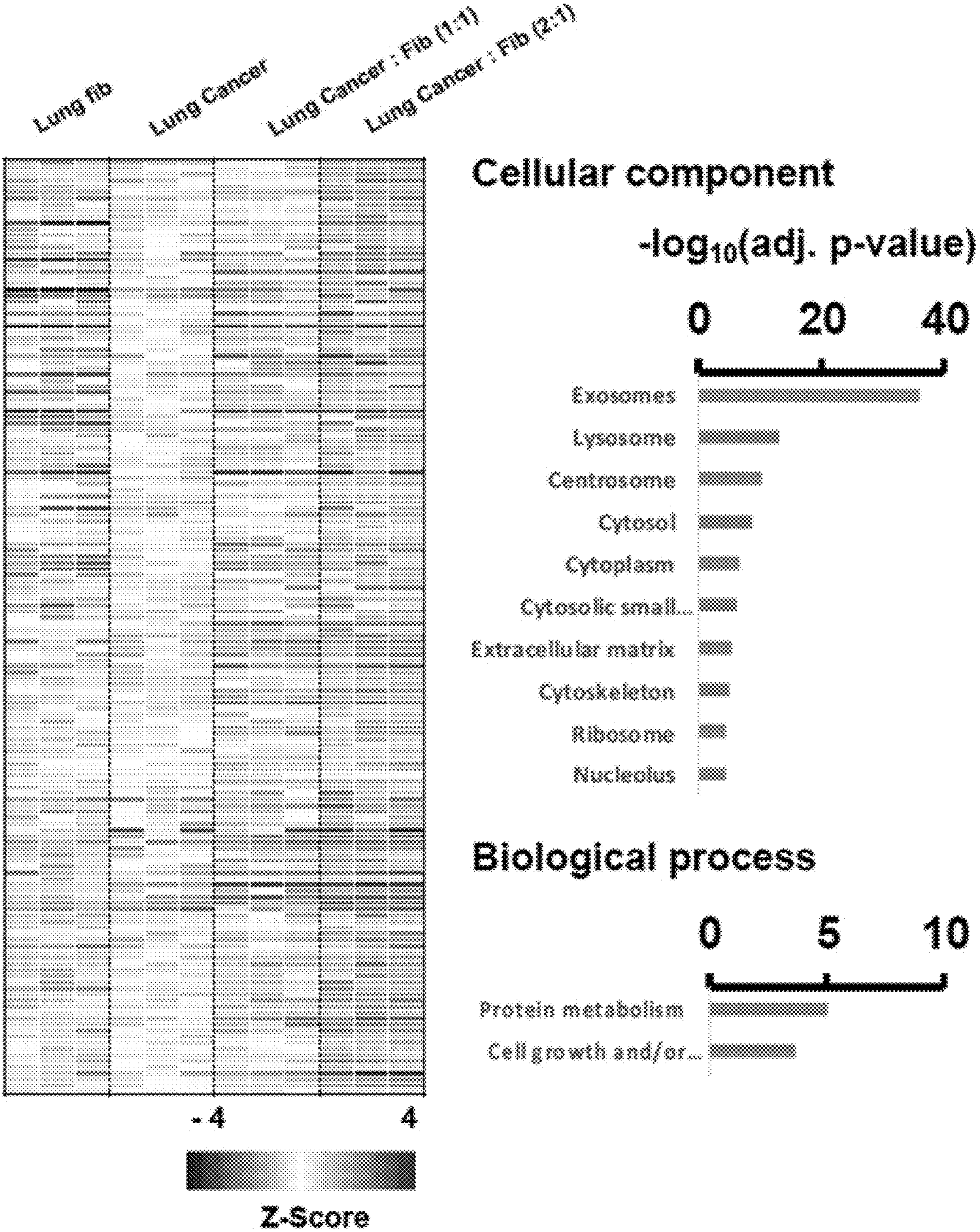
FIG. 7 illustrates proteomic comparison of exosomes isolated from monocultures and cocultures of lung fibroblasts and lung cancer cells.
Figure 8:
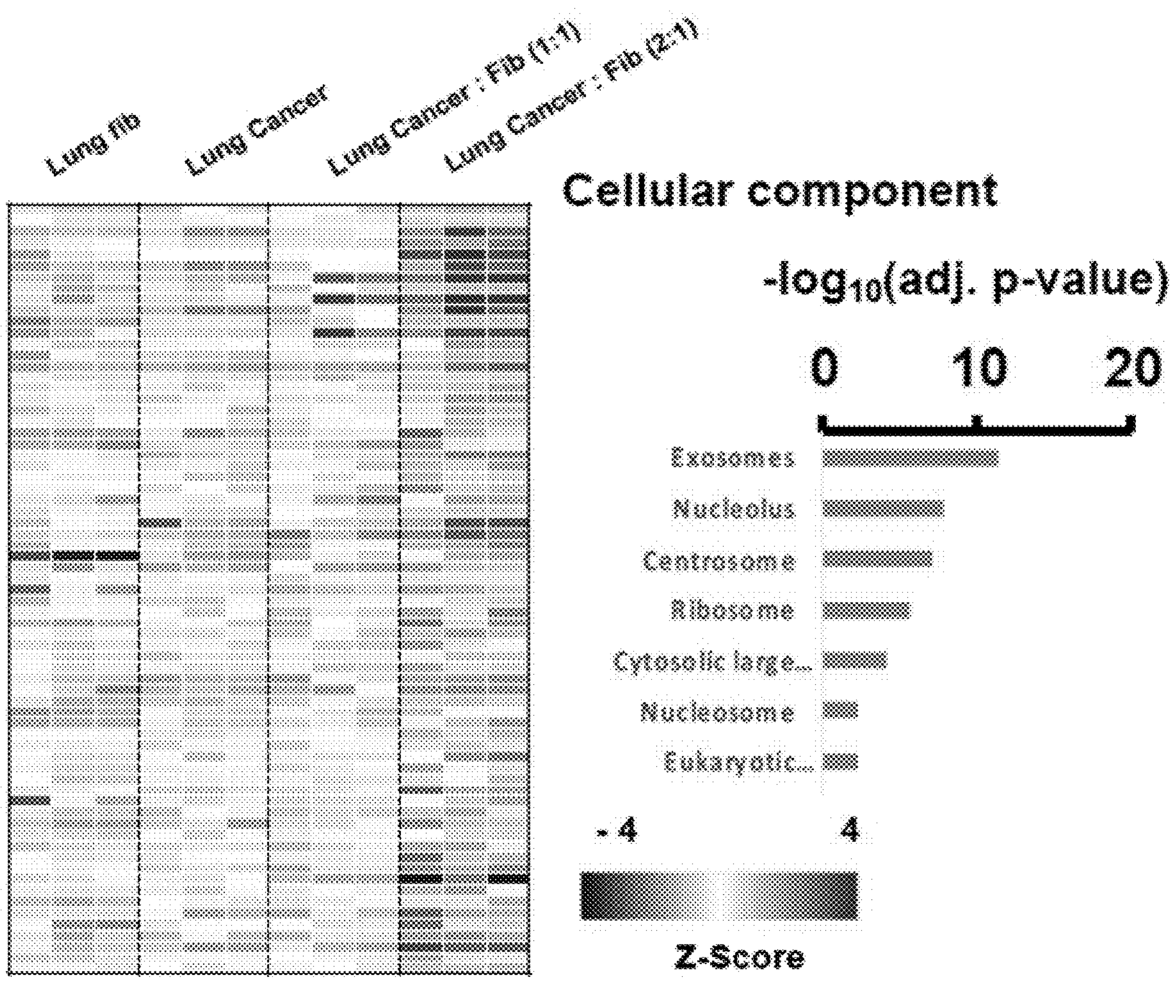
FIG. 8 illustrates proteomic comparison of intracellular vesicles isolated from monocultures and cocultures of lung fibroblasts and lung cancer cells.
Figure 9:
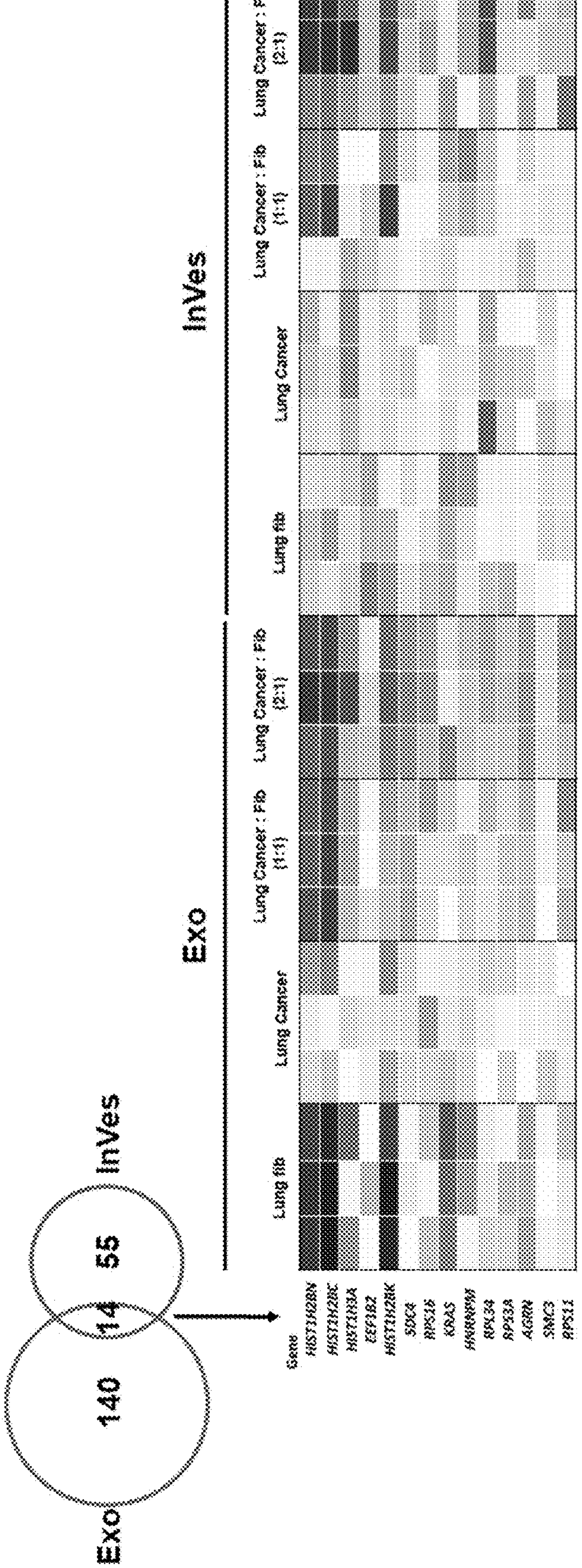
FIG. 9 illustrates proteomic comparison of exosomes and intracellular vesicles isolated from monocultures and cocultures of lung fibroblasts and lung cancer cells in different ratios.

A new exosome isolation and sorting technology capable of isolating unique exosome subsets has been created that is designed to be scalable and translatable, low-cost, easy to use and compatible with available microfluidics set-ups. MEFS is a technical innovation in the field of exosome research as it proposes to overcome a technological barrier that has limited efforts to sort exosome subsets. Additional to these, an Auto-MFES device has been designed to house multiple MFES chips to automatically sort exosomal subpopulations as illustrated in FIG. 2. This system can be potentially repurposed for other applications such as the study of thrombosis, vasculitis and systemic cardiovascular disorders, such as coronary artery disease and hyperlipidemia in which abnormal exosome biology also plays a major pathogenic role since exosomes, microvesicles and other extracellular vesicles can carry enriched biomarkers that might be early indicators of diseases including cancer, cardiac diseases, renal disease, hepatic disorders.

Example II: Isolation of Intracellular Vesicles from Cells and Comparison with Exosomes Cells secrete vesicles to the extracellular space in vitro and in vivo to their surroundings. Given that there are multiple mechanisms for cells to secrete these vesicles as reported in the literature, it is meaningful to examine the differences in the vesicles within the cells. Methods and protocols are implemented to isolate the inner components of cells. These inner components include vesicles, organelles (such as lysosomes), and other inner components of the cells that may have lipid bilayers.

The steps for the isolation of intracellular vesicles and organelles of the cells follow these steps:

Cells cultured using culture media supplemented with 10% fetal bovine serum (FBS) until they reach confluency. Then, the cells will be washed with PBS (3×) and cultured for an additional two days using culture media supplemented with 5% exosome depleted FBS for 48 hours.

After 48 hours, culture media was harvested and centrifuged at 500 g for 5 minutes to separate the cells and at 2000 g for 20 minutes to separate remaining cell debris. Remaining supernatant was processed as is described in Liu F, Vermesh O, Mani V, et al. "The Exosome Total Isolation Chip." ACS Nano 2017; 11. Cells that have been cultured adherent to the flask were trypsinized and pelleted at 500 g for 5 minutes. Then, the pellet was frozen at −20° C. and thawed at room temperature sequentially for three times to breakdown the cell membrane and obtain inner components of the cells. The obtained cell debris, organelle, intracellular vesicle suspension was diluted with PBS, filtered through a 0.22 μm syringe type filter to remove bigger cell debris and processed through ExoTIC (see, e.g., U.S. patent application publication no. 2019/0049438). After that, both an extracellular suspension isolated from the culture media (Exo) and intracellular vesicles (InVes) isolated from frozen-thawed cell suspensions from monocultures and co-cultures with different cell ratios were analyzed.

The isolated exosomes (Exo) and intracellular vesicles (InVes) were re-concentrated using a centrifugal concentrator to decrease the sample volume easing the downstream analysis. These vesicles were first quantified using Nanoparticle Tracking analysis (NTA) as given in FIGS. 3*a*-*f* with size profiling for Exo and InVes and peak sizes, with concentrations. Then, to validate the origin of the isolated Exos and InVes', samples also has been analyzed through a rigorous proteomic pipeline. Comparative data from these analyses can be found in FIGS. 4-9.

Example III: Exosome Enrichment from Plasma and Tissue Samples in a Pre-Clinical Pancreatic Cancer Model A novel approach is provided for the isolation of exosomes from tissues and small volumes of plasma. By leveraging this unique capability, it is demonstrated that exosomes both from plasma and tissue samples can be isolated from a pancreatic ductal adenocarcinoma (PDAC) mouse model with high yield. Proteomic analysis of exosomes isolated from tissue samples identified known exosome cancer markers such as EPCAM, CD82, CD26, and integrins. In addition, we identified several additional human proteins which are important in cancer, including carcinoembryonic antigens cell adhesion molecules (CEACAM1, CEACAM6) and mucins (MUC1, MUC13) in all of the exosome samples. The ability to efficiently isolate exosomes from small sample volumes creates new avenues for pre-clinical studies in small live-animal tumor models, and for point-of-care exosome-based clinical studies from small sample volumes (10-100 μL).

Pancreatic cancer is a lethal malignancy accounting for 3% of all cancers and 7% of all cancer deaths in the US, with an average lifetime risk of developing this disease at 1 in 67 people. The 5-year survival rate is very poor at 6%, with a median survival rate of only 6 months. Most pancreatic cancers (95%) arise from the exocrine component of the pancreas and are of adenocarcinoma histology, otherwise known as pancreatic ductal adenocarcinoma (PDAC). The poor prognosis of pancreatic cancer relates to its late presentation, predominantly due to difficulty in early detection; high metastatic potential, and resistance to conventional therapies. The pancreas is situated deep within the abdomen, which makes sampling suspicious areas with a tissue biopsy technically challenging and not without considerable risk. For decades, the ability to efficiently screen for pancreatic cancer in high-risk patients, with high sensitivity and specificity, has eluded both physicians and scientists. Due to the limited treatment options, the early presence of metastases, and technical difficulty in surgically resecting the pancreas, it is appealing to develop a liquid biopsy for pancreatic cancer. However, the ability to identify circulating biomarkers with high sensitivity and specificity for pancreatic cancer has been challenging. Clearly, there is an unmet clinical need for developing enabling tools that will broadly facilitate reliable and non-invasive biomarkers in tissues or when small sample volumes are available from small animals or using rare and precious bio-banked human samples. Development of such tools would contribute to discoveries for early detection of pancreatic cancer for appropriate medical intervention.

A major roadblock in extracellular vesicle research is the lack of robust, standardized, reproducible, efficient, and reliable methods for isolating high-purity EVs and exosomes with high yield. Existing EV isolation technologies such as, ultracentrifugation, multi-step filtration, antibody-conjugated magnetic beads, and polyethylene glycol-based precipitation, are costly and/or time consuming. There is also a lack of available standardized technologies and protocols to isolate exosomes from tissue samples or handle small sample volumes (<100-200 μL), as existing methods often suffer from poor yields and unpredictable purity, especially when applied to plasma or serum. These limitations make standardization difficult and prove to be ineffective for processing precious and limited samples often needed in clinical applications and available from large clinical trials. Although immunocapture-based exosome isolation methods can collect exosomes with moderate to high purity, these suffer from multi-step, multi-hour, and tedious processing, limiting their broad applicability. To overcome some of these critical technological hurdles of exosome isolation, a cost-effective exosome total isolation chip (ExoTIC, see references above) has been provided for isolating exosomes with high-yield from a wide range of clinical biofluids, such as plasma, serum, saliva, urine, and lavage. It is also contemplated that isolation could also be performed on other biofluids, such as, for example, tears and sweat. However, despite the demonstrated broad applicability to a variety of sample types, there has been minimal assessment of the platform for a comprehensive evaluation on tissue samples and its applicability to small sample plasma volumes (~100 μl). There are multiple methods reported in the literature for isolating exosomes. There have also been recent efforts to perform exosome isolation from tissues using commercially available methods; however, these attempts do not represent repeatable and reproducible results, suffering from unestablished working protocols. Moreover, they have shown limited applications in clinically-relevant cancer samples and complex biological matrices, and their downstream molecular analysis do not present the agreement of exosomal proteins in the tissues with circulating exosomes in the blood in a pre-clinical cancer model.

Figure 10A:
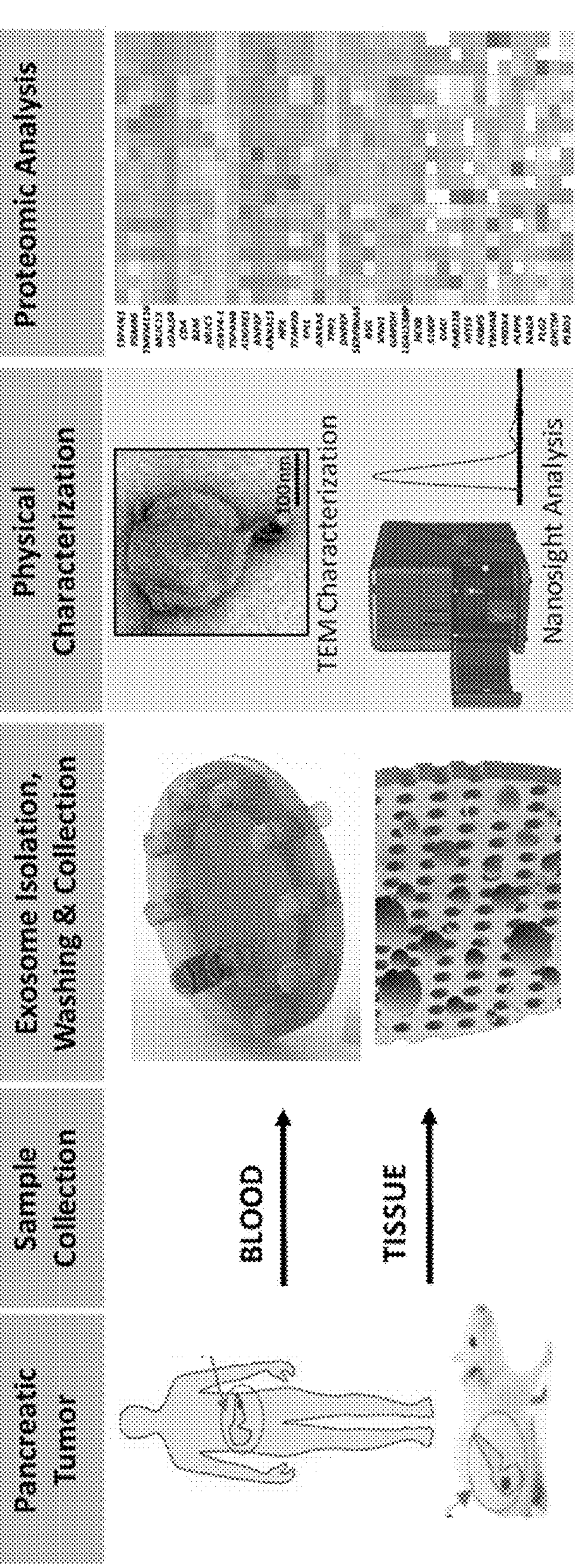
FIGS. 10A-D illustrate a mechanical nano-filtration and enrichment of exosomes from plasma and primary tumor tissue samples from an orthotopic mouse model of human PDAC, with the ExoTIC platform.
Figure 15:
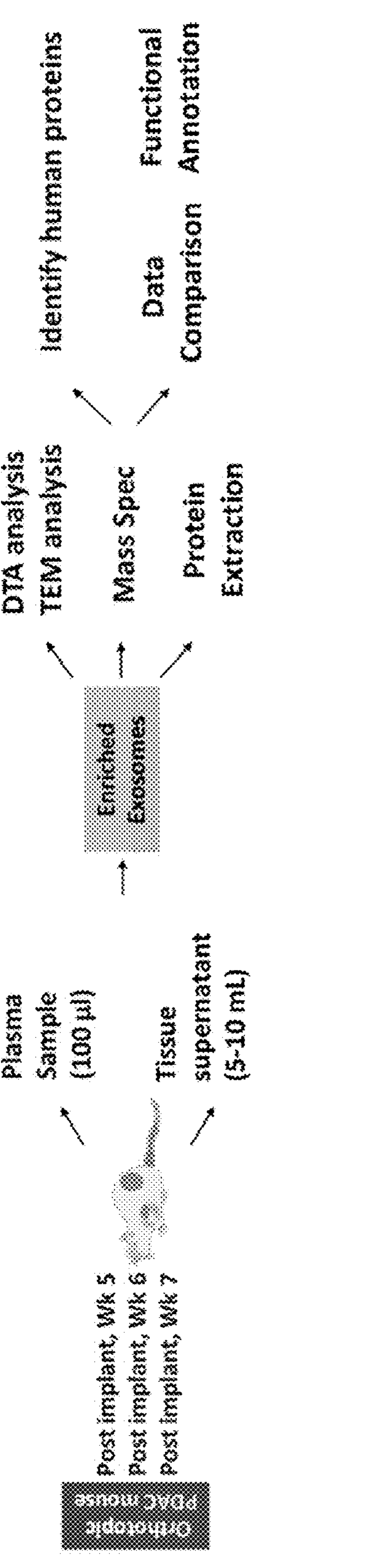
FIG. 15 is a workflow of sample processing for exosome isolation from mouse plasma and tissues. The enriched extracellular vesicles are collected through our tool and used for physical characterization and downstream proteomic analysis.

In this example, the application of a new tool to isolate and investigate exosomes released into the bloodstream from primary pancreatic tumors in an orthotopic mouse model of human PDAC is described. Using this novel approach, the relationship can be studied between certain proteins found within the blood plasma and how they relate with exosomal proteins found in the primary pancreatic tumor tissue (FIG. 10A and FIG. 15). First, an orthotopic mouse model of human PDAC is employed and, working with this pre-clinical model, it is shown that exosomes can be isolated from 100 μl of mouse plasma and pancreatic cancer tissue samples (<1 $mm^3$ in size) using the total exosome isolation chip (ExoTIC). Finally, a proteomics analysis is performed to demonstrate the identification of human proteins in exosome samples isolated both from tissue and plasma samples collected from the orthotopic mouse model. This strategy uniquely enables comparison of the changes in protein expression of exosomes in two-dimensional (2D) cell culture, as well as three-dimensional (3D) tumor microenvironment once implanted in the mouse model and in the bloodstream. Furthermore, given the limitations of small sample volumes available from the mouse model, this tool enabled a unique study to obtain and analyze exosomes from longitudinal blood samples from mice. This is believed to be the first study to describe a protocol to enrich exosomes from ex vivo tumor specimens and compare their content to the exosomes in circulation. The approach builds a broadly applicable, standardized tool for exosome isolation from plasma and tissue samples with very small volume; and identifies potentially interesting exosome-related proteins in pancreatic cancer.

Mechanical Nano-Filtration and Isolation Exosomes with ExoTIC Platform

Figure 10B:
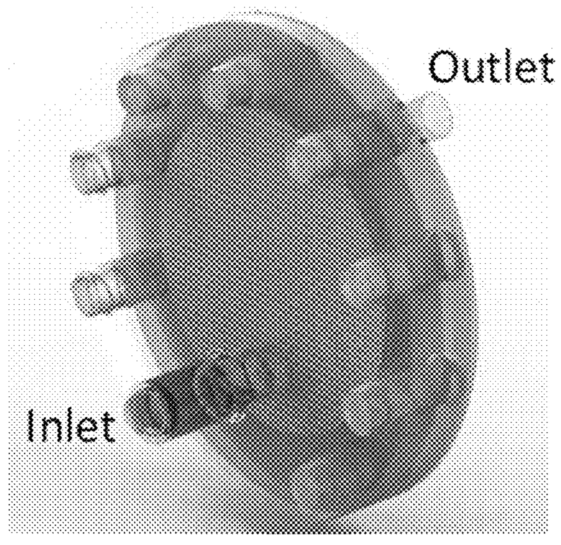
Figure 10D:
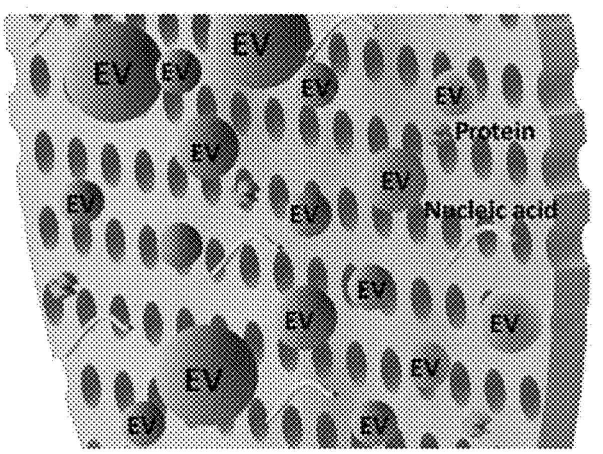
Figure 10C:
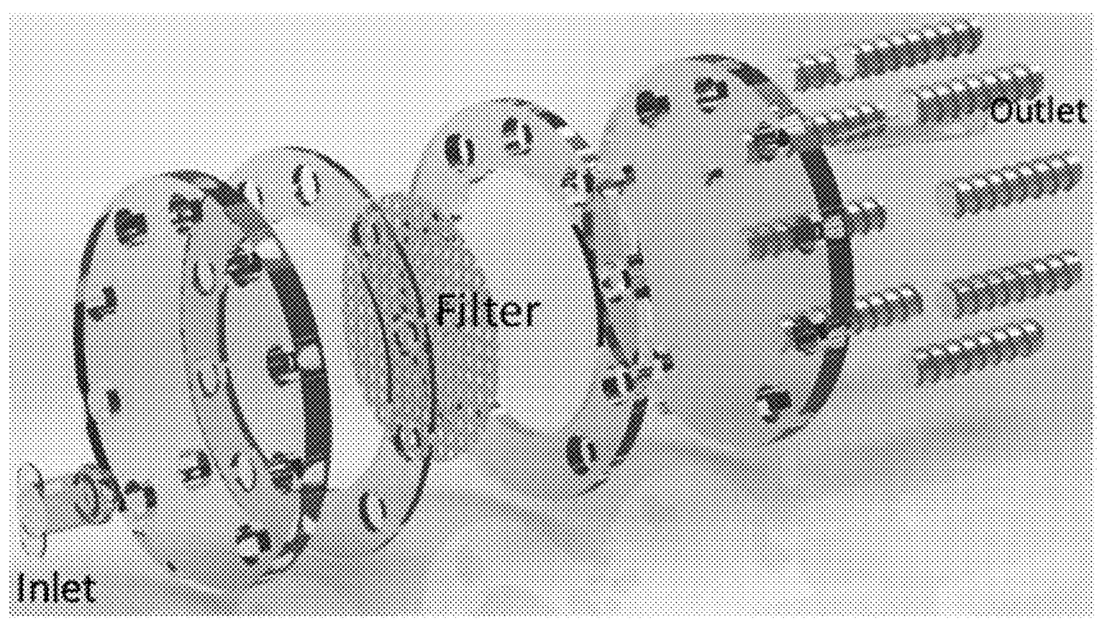

The ExoTIC platform is designed to enable enrichment of exosomes from cell culture media, plasma, and tissue samples. It comprises multiple layers, such as: poly (methyl methacrylate) (PMMA), a nanoporous low-protein-binding filter membrane, a paper pad, screws, and nuts (FIGS. 10B and 10C). The pore size of the ExoTIC nano-filter membrane is fine-tunable, which uniquely enables size-based sorting of exosomes. It has been reported in the literature that exosomes with different sizes carry differential biological cargo with different composition. In this example, vesicles in 50-200 nm size range are focused on to investigate the changes in their protein cargo during disease progression, rather than microvesicles (>200 nm) or even bigger vesicles. Therefore, a 50-nm nano-filter membrane was used to isolate the exosomes. Before introducing the plasma or tissue samples into the ExoTIC platform, each sample was first pre-filtered with a 220-nm membrane to remove cells, potential bacterial contaminants, and other larger cellular fragments. Then, the sample was loaded through the inlet at a flow rate of 5 mL/hour. Small molecules, such as nucleic acids and proteins, passed through the outlet of the ExoTIC filter membrane while exosomes were retained in the chamber in front of the filter membrane (FIG. 10D). After passing through the filter, exosomes were concentrated at the outlet. As a regular step for exosome isolation using this tool, the concentrated exosomes in front of the tracked-etched membrane, were washed by the introduction of PBS through the platform to minimize the contamination and to remove all the plasma components. The exosomes isolated and washed with this tool were highly concentrated at a volume of ~400 μL in washing buffer which was defined by the retention chamber volume of the device. After this concentration step, isolated exosomes can be harvested with a simple micropipetting step.

Orthotopic Model of Human PDAC in Mice

Figure 11A:
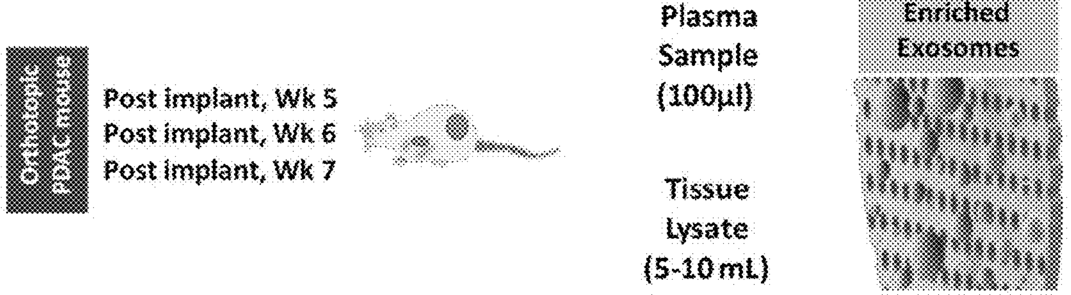
FIG. 11A-C illustrate an orthotopic PDAC mouse model.
Figure 11B:
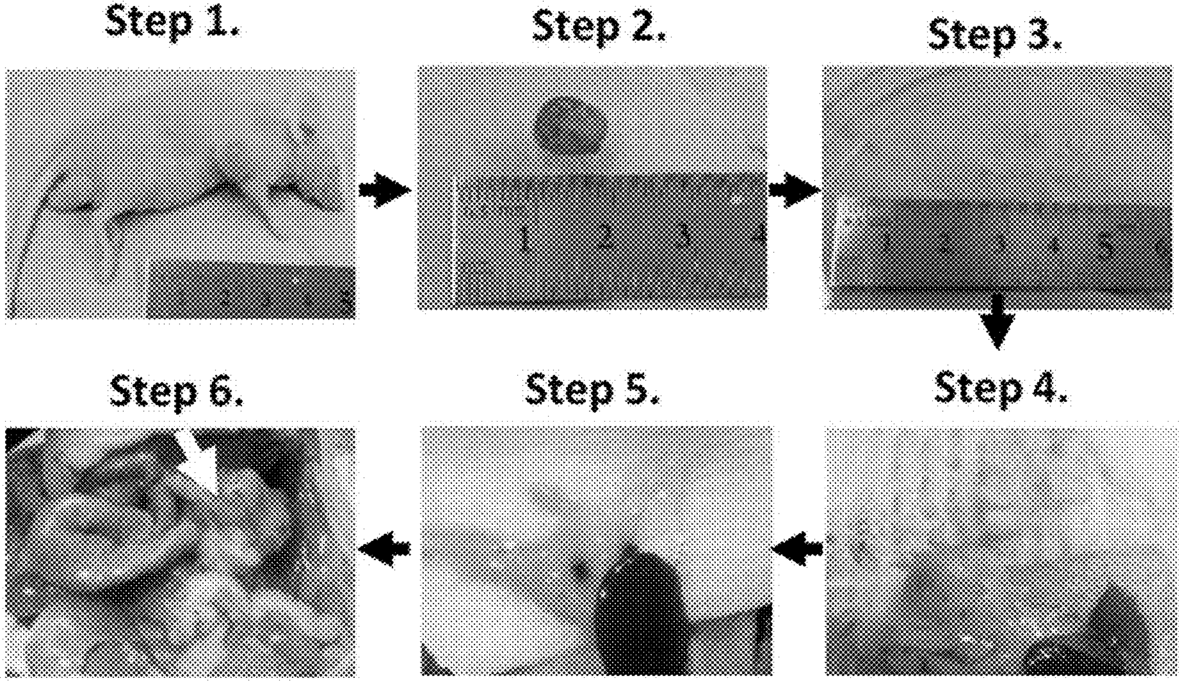
Figure 11C:
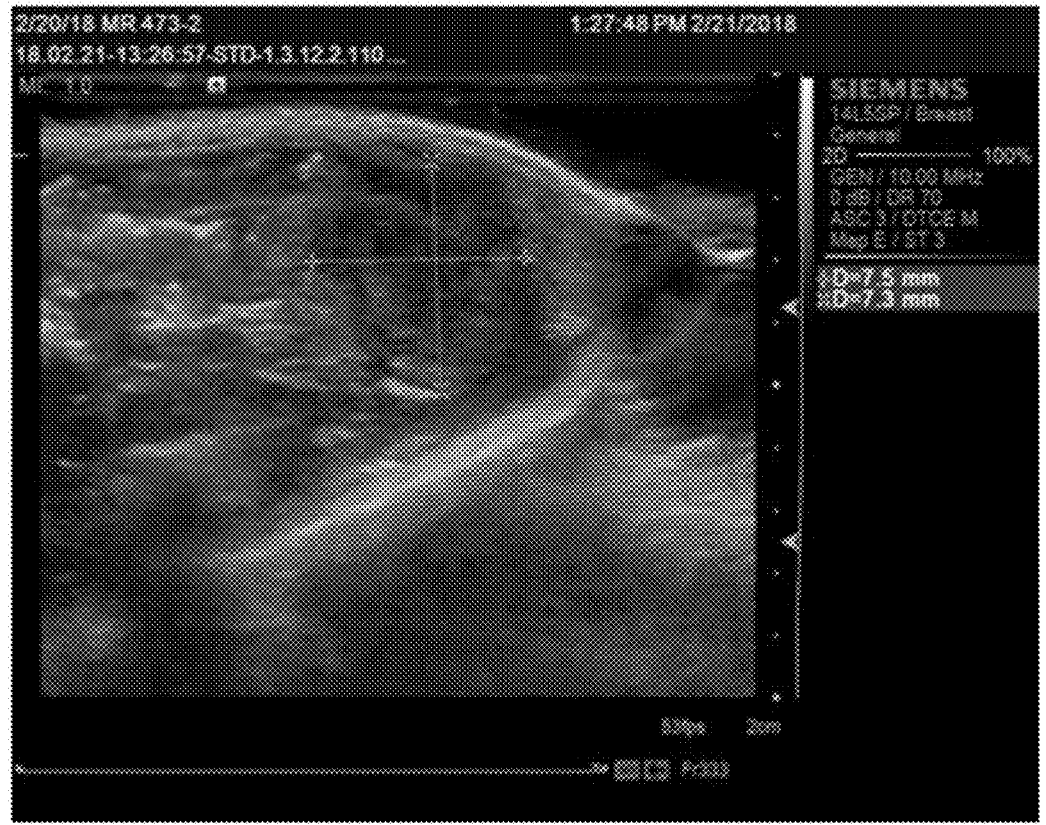

In a small animal cohort, an orthotopic model of human PDAC in mice using human AsPC-1 pancreatic carcinoma cells was employed (FIGS. 11A-C). Compared to the xenograft models, orthotopic models of pancreatic cancer better simulate human disease given their ability to locally infiltrate into adjacent structures, including the liver and peritoneum, in addition to animals developing ascites and cachexia in the late disease stages (i.e., weeks 6-7 in mice). The use of a mouse model allowed serial blood sampling for longitudinal exosomal analysis for the study (FIG. 15). Once implanted in the recipient mouse, the human AsCPC-1 pancreatic cancer cells developed poorly differentiated tumors of adenocarcinoma histology and surrounding stromal reaction, similar to human disease. In addition, the tumors grew rapidly with metastases often seen to the liver, spleen and peritoneum at late stages, as often seen in human patients.

Figure 12A:
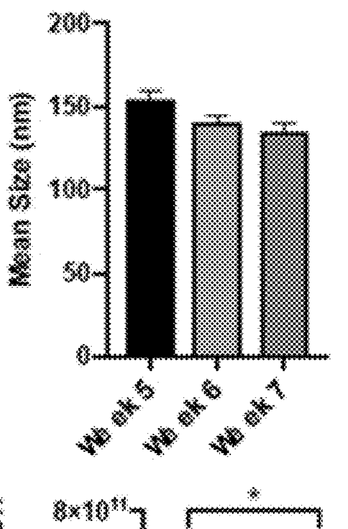
FIGS. 12A-D provide data relating to the isolation and physical characterization of exosomes from human PDAC mouse tissue and plasma samples.
Figure 12A:
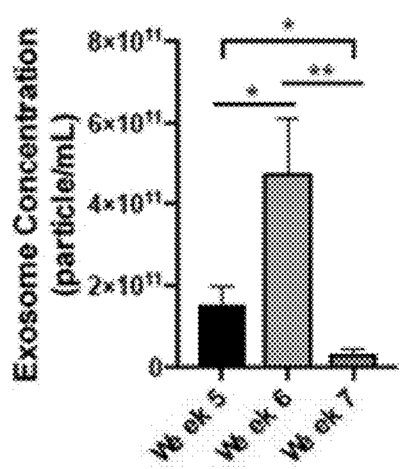
Figure 12A:
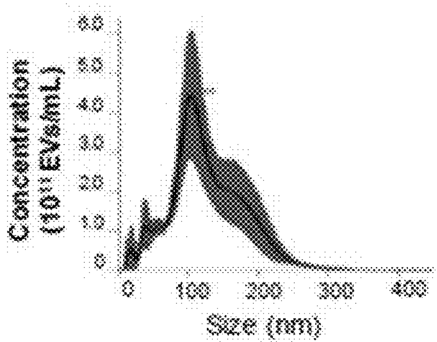
Figure 12B:
Figure 12B:
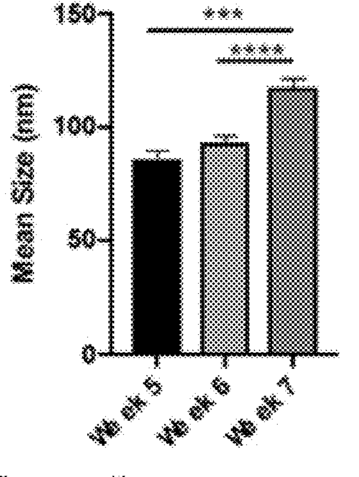
Figure 12B:
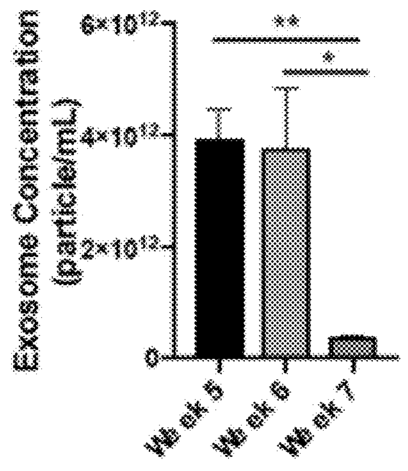
Figure 12B:
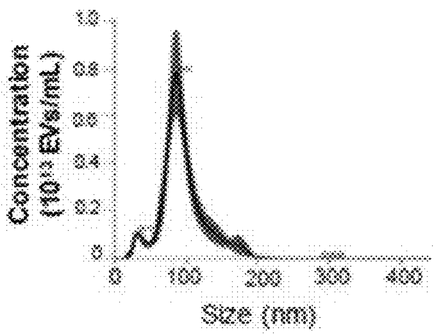
Figures 12C, 12D:
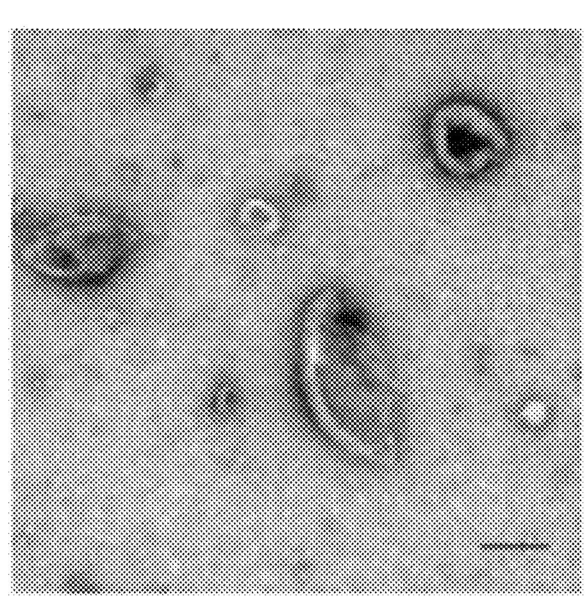
Figure 16:
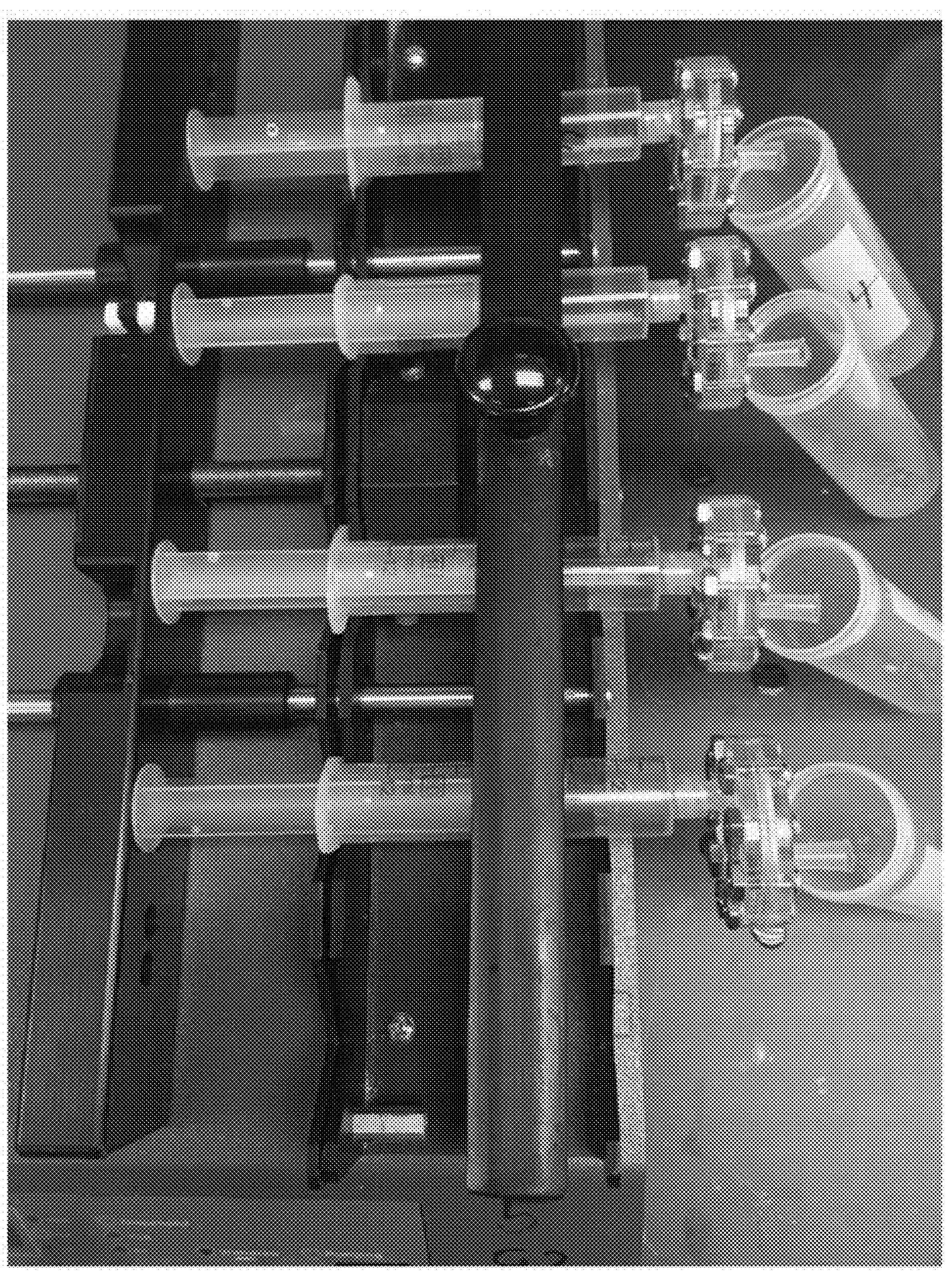
FIG. 16 is an ExoTIC device for isolation of exosomes from multiple samples in parallel to allow processing of larger or multiple samples simultaneously.
Figure 19A:
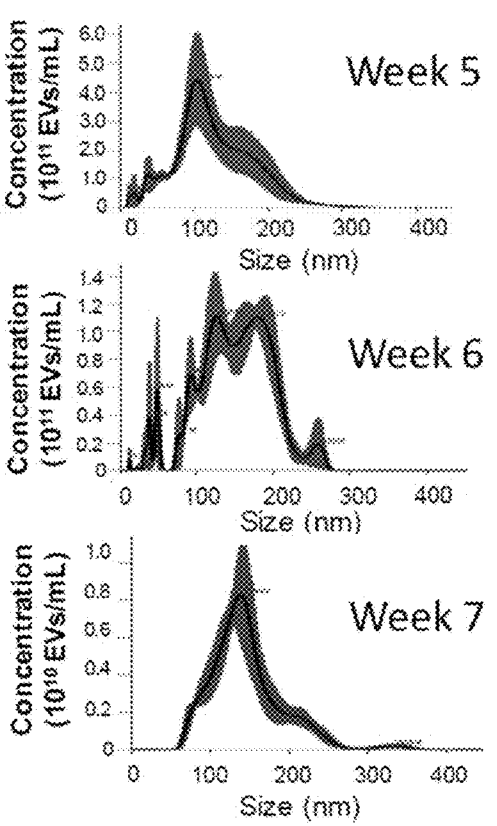
FIG. 19A illustrates NTA analysis of exosomes isolated from tissue samples after 5, 6, and 7 weeks of pancreatic tumor implantation, respectively
Figure 19B:
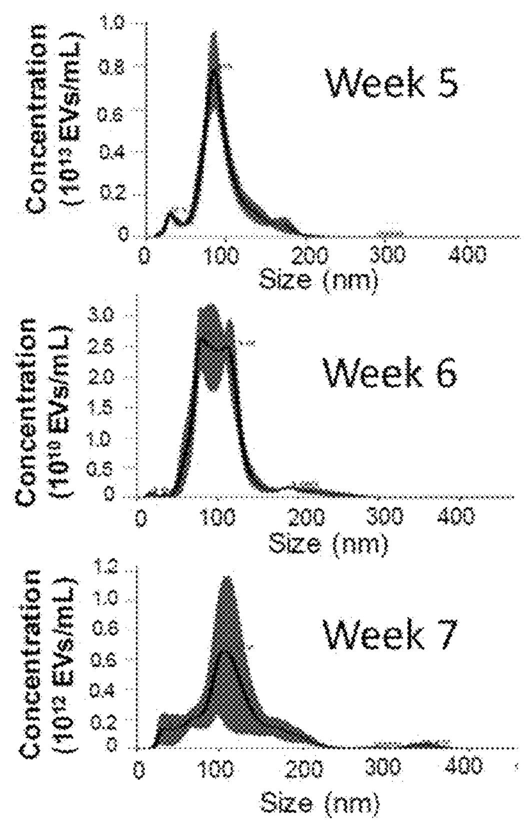
FIG. 19B illustrates NTA analysis on of exosomes isolated from 100 μl plasma after 5, 6, and 7 weeks of pancreatic tumor implantation, respectively.
Figure 20:
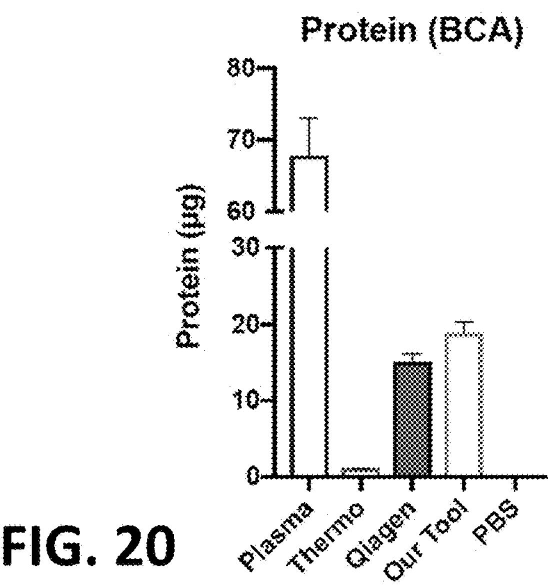
FIG. 20 illustrates protein quantification comparison of plasma and plasma derived exosomes using commercial kits and our tool.

Isolation and Physical Characterization of Exosomes from Human PDAC Mouse Tissue and Plasma Samples Next, in a small pilot animal cohort, the physical properties of exosomes released into the bloodstream from primary pancreatic tumors in the orthotopic PDAC model were investigated. To date, most analyses on the role of exosomes in healthy and diseased states have relied on studying the vesicles from in vitro sources, such as conditioned cell culture media, or body fluids (e.g., sweat, tears, lavage, serum, plasma, or urine). It has been reported that small amounts of exosomes are present in tissues. The direct analysis of these bodies and their cargoes by downstream 'omics' technologies depend on the isolation and enrichment strategies that can reduce the background soluble proteins, proteinaceous aggregates, and proteolytic contaminants. Thus, an in-house developed tool was utilized to isolate exosomes from both mouse primary tumor tissue and plasma samples (FIG. 12A-C). 100 μl of plasma was collected from the same mouse for weeks 5, 6 and 7 after tumor implantation. The mouse plasma samples was processed using our tool to isolate exosomes. In addition, in another animal cohort, orthotopic mice were sacrificed and the primary pancreatic tumors were harvested for weeks 5, 6 and 7 after implantation. 250-1,000 μg of pancreatic cancer tissue sample (i.e., primary tissue) was isolated from each mouse. Tissue samples were then digested with DNase-1. The resulting tissue homogenate was sequentially diluted with PBS, filtered through a 70 μm mesh filter and a 220-nm syringe filter before processing for exosome isolation. Multiple samples were run in parallel to allow processing of pre-clinical samples simultaneously (FIG. 16). Mean size and concentration of exosomes isolated from tissue and plasma samples were compared using Nanoparticle tracking analysis (NTA) (FIGS. 12A-C). Exosomes isolated from tissue samples had mean size values of 153.55±5.84 nm, 140.6±4.1 nm and 134.45±5.33, where the concentrations were $1.53*10^{11}±4.51*10^{10}$, $4.73*10^{11}+1.38*10^{11}$, and $3.37*10^{10}±9.57*10^{9}$ for weeks 5, 6 and 7, respectively with a heterogeneous size distribution profile (FIG. 12A). Exosomes isolated from the plasma samples had mean size values of 85.47±4.05 nm, 93.35±2.42 nm and 117.0±4.25, where the concentrations were $3.93*10^{12}±5.48*10^{11}$, $3.79*10^{12}±1.04*10^{12}$, and $3.71*10^{11}±4.35*10^{10}$ for weeks 5, 6, and 7, respectively with a more homogenous size distribution profile (FIG. 12B). Interestingly, the mean size of the plasma exosomes significantly increased at week 7 (week 5-7, p=0.0006; week 6-7, p<0.0001). In addition, the average tumor size increased from ~6 mm at week 6 to ~50 mm at week 7. This suggests that size of exosomes can potentially be a determinant factor for their possible uptake by neighboring cells and their functionality during cancer progression and metastasis. In addition, the NTA data obtained from two different sample types was compared: plasma and tissue (FIG. 12C). The exosomes isolated from tissue samples were significantly bigger in size compared to the counterparts isolated from plasma (p=0.0005). Conversely, the plasma exosomes were more abundant (p<0.0001) in suspension after isolation and washing step. Transmission electron microscopy (TEM) imaging analysis of the exosomes isolated from tissue samples detected exosomes; ranging in size from 50 to 150 nm. No other structures, aggregates or impurities were observed with TEM, confirming their purity (FIGS. 12D and 17A). Immunogold labelling with a CD63 antibody visualized by TEM further confirmed the presence of exosomes (FIG. 17B). Representative nanoparticle tracking analysis are shown in FIGS. 12A-D and 18A-B). Representative nanoparticle tracking analysis of exosomes isolated from tissue and plasma samples after 5, 6, and 7 weeks of pancreatic tumor implantation, are shown in FIGS. 19A-B, respectively.

Proteomic Analysis of Tissue, Plasma, and Cell-Derived Exosomes

Figure 13A:
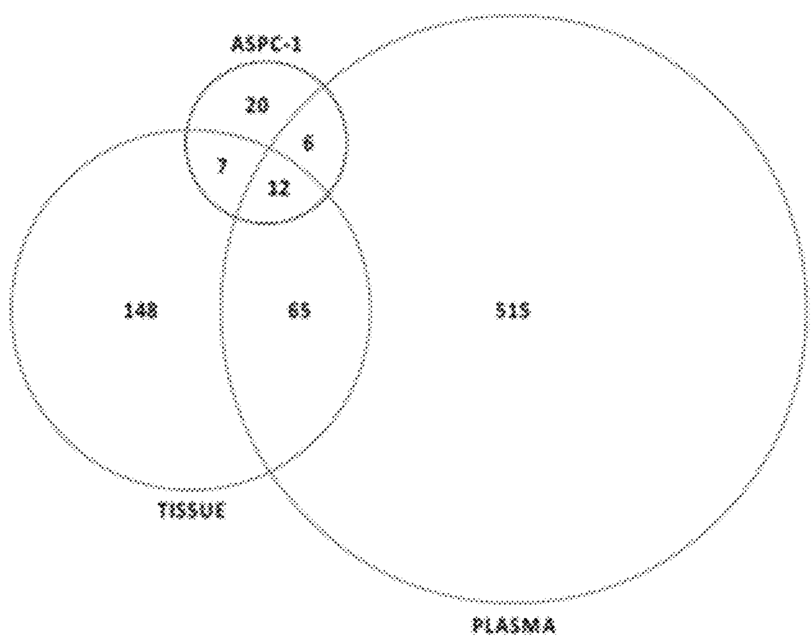
FIGS. 13A-E illustrate a proteomic analysis of human proteins identified in exosomes from the PDAC mouse model.

Next, proteomic analysis was performed on the exosomes collected from plasma and tissue samples to specifically identify human proteins from exosomes collected from the orthotopic PDAC mice. In addition, exosomes were collected from the culture media of human AsPC-1 cancer cells. This enabled comparison of the changes in protein cargo of exosomes in two dimensional cell culture, as well as three-dimensional (3D) tumor microenvironment once implanted in mouse model and in bloodstream. Protein database searches resulted in the identification of 598, 232, and 45 unique human proteins from tissue, plasma, and AsPC-1 cell derived exosomes, respectively, as shown in the Venn diagram (FIG. 13A). Among them 82, 78, and 72% of proteins have been previously described as expressed in the pancreas in HPRD, Uniprot, and Human Protein Atlas. This percentage increased to 86% when the proteins were required to be identified in at least two sources.

Figure 13B:
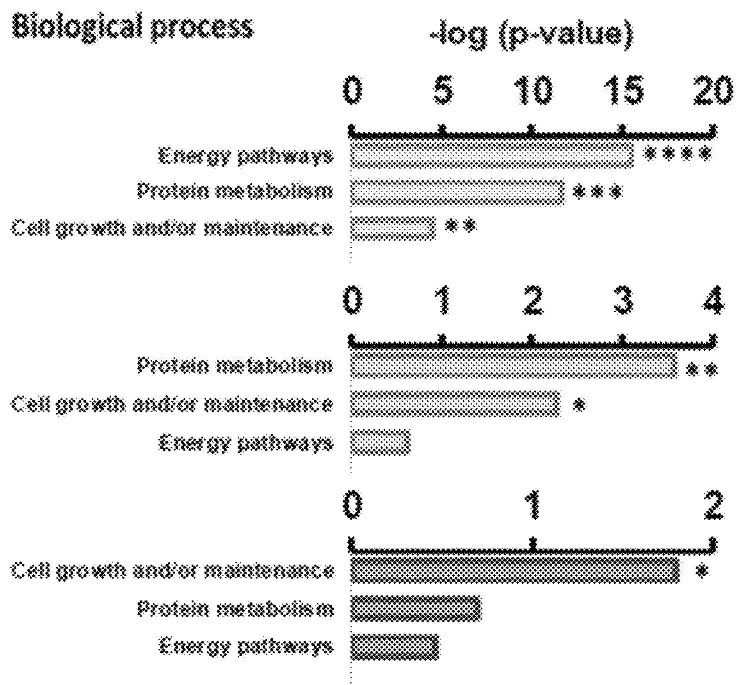
Figure 13C:
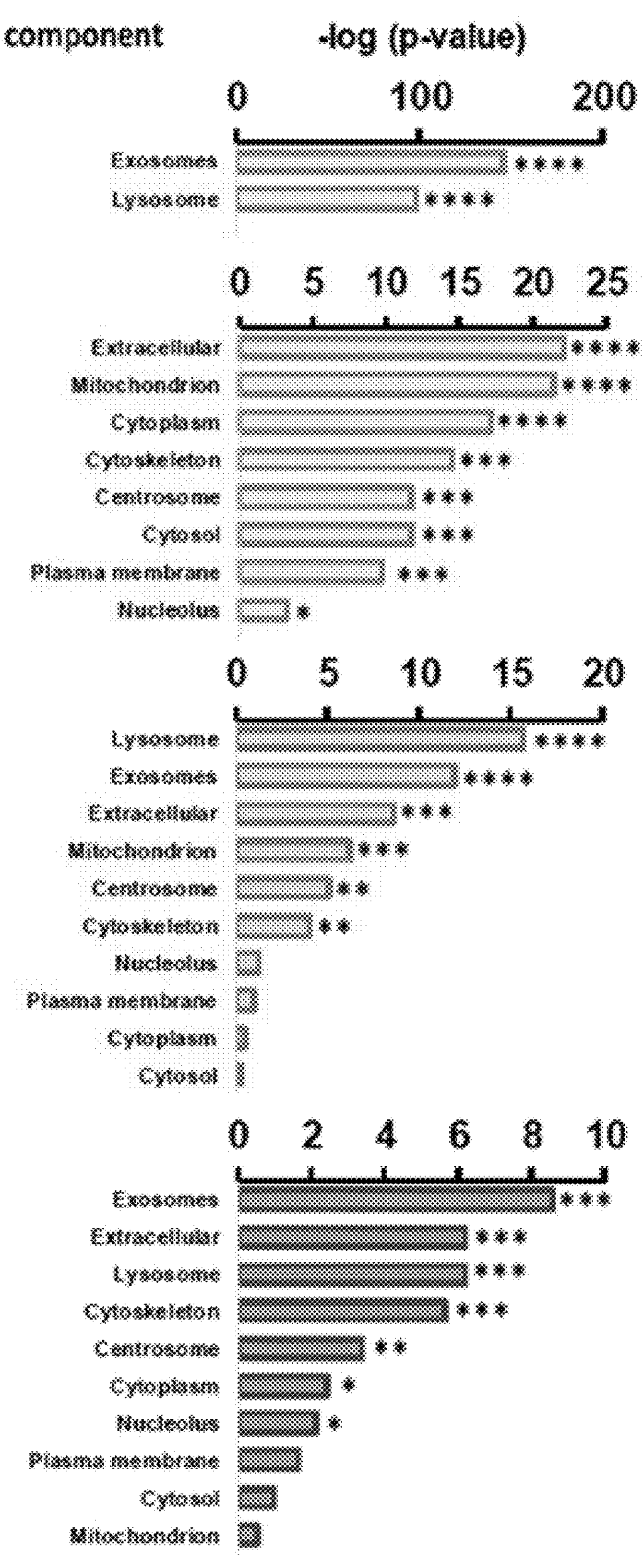
Figure 13D:
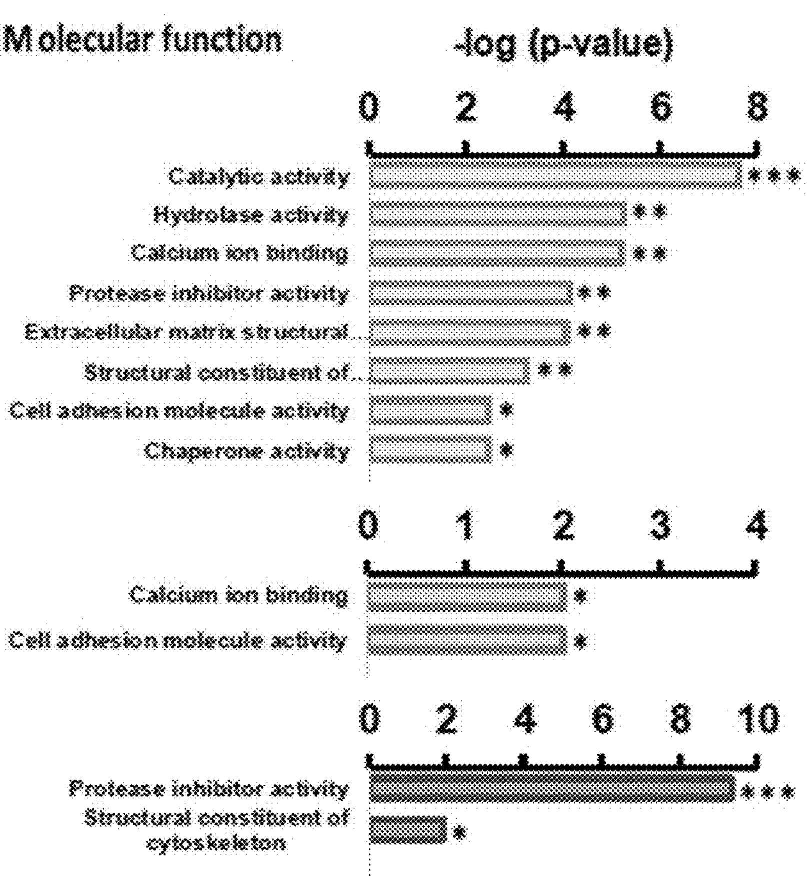
Figure 13E:
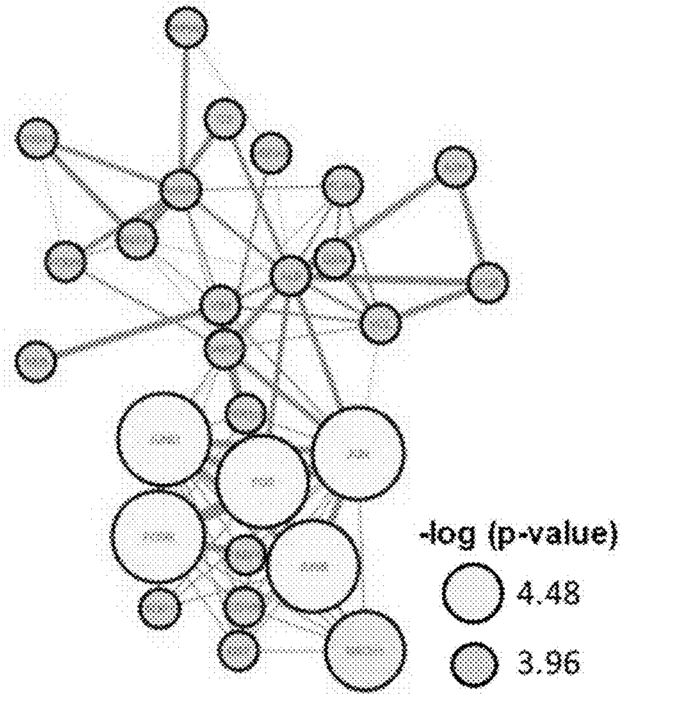
Figure 14A:
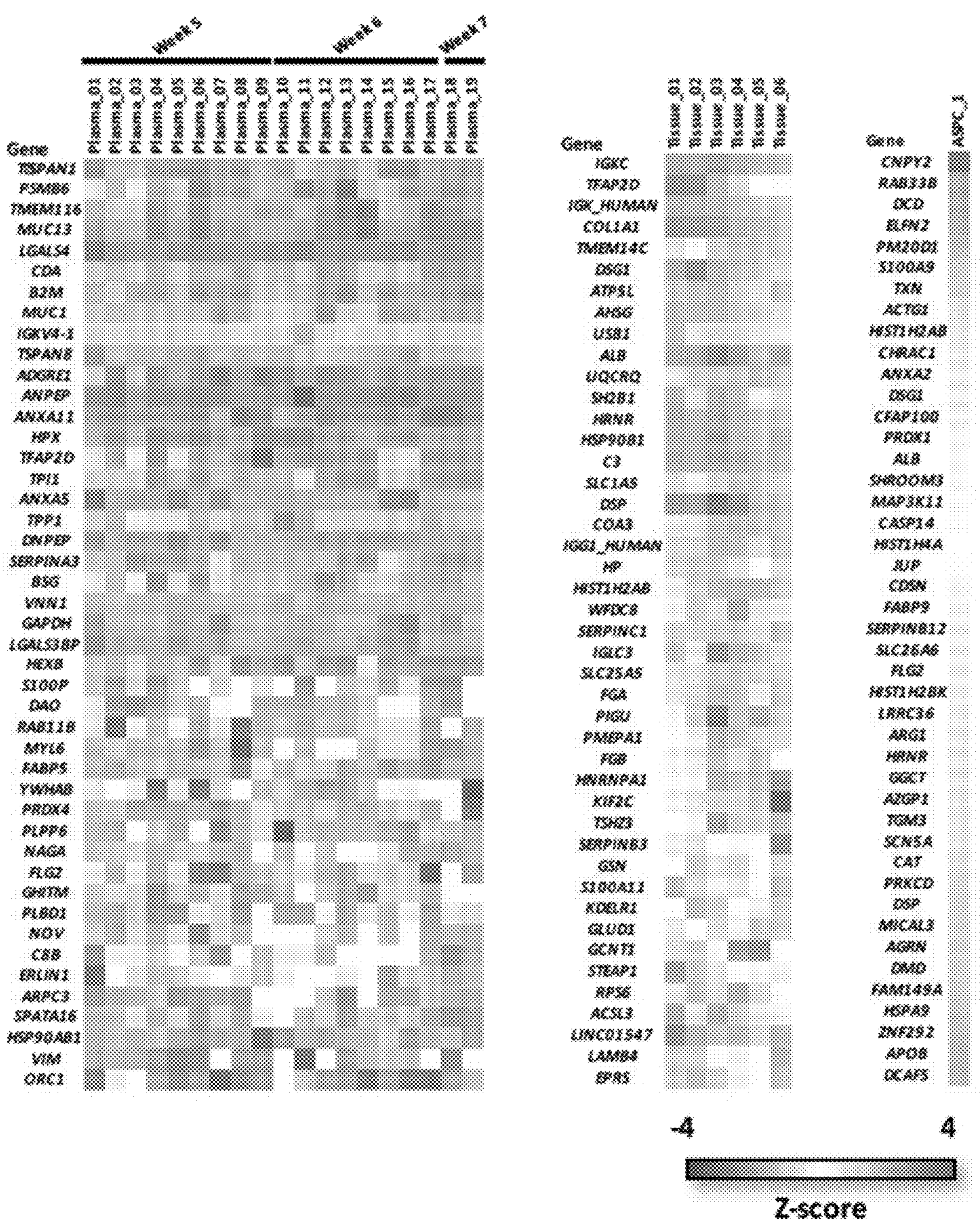
FIGS. 14A-B are quantitative proteomic analysis of human pancreatic cancer implants-derived exosomes.
Figure 14B:
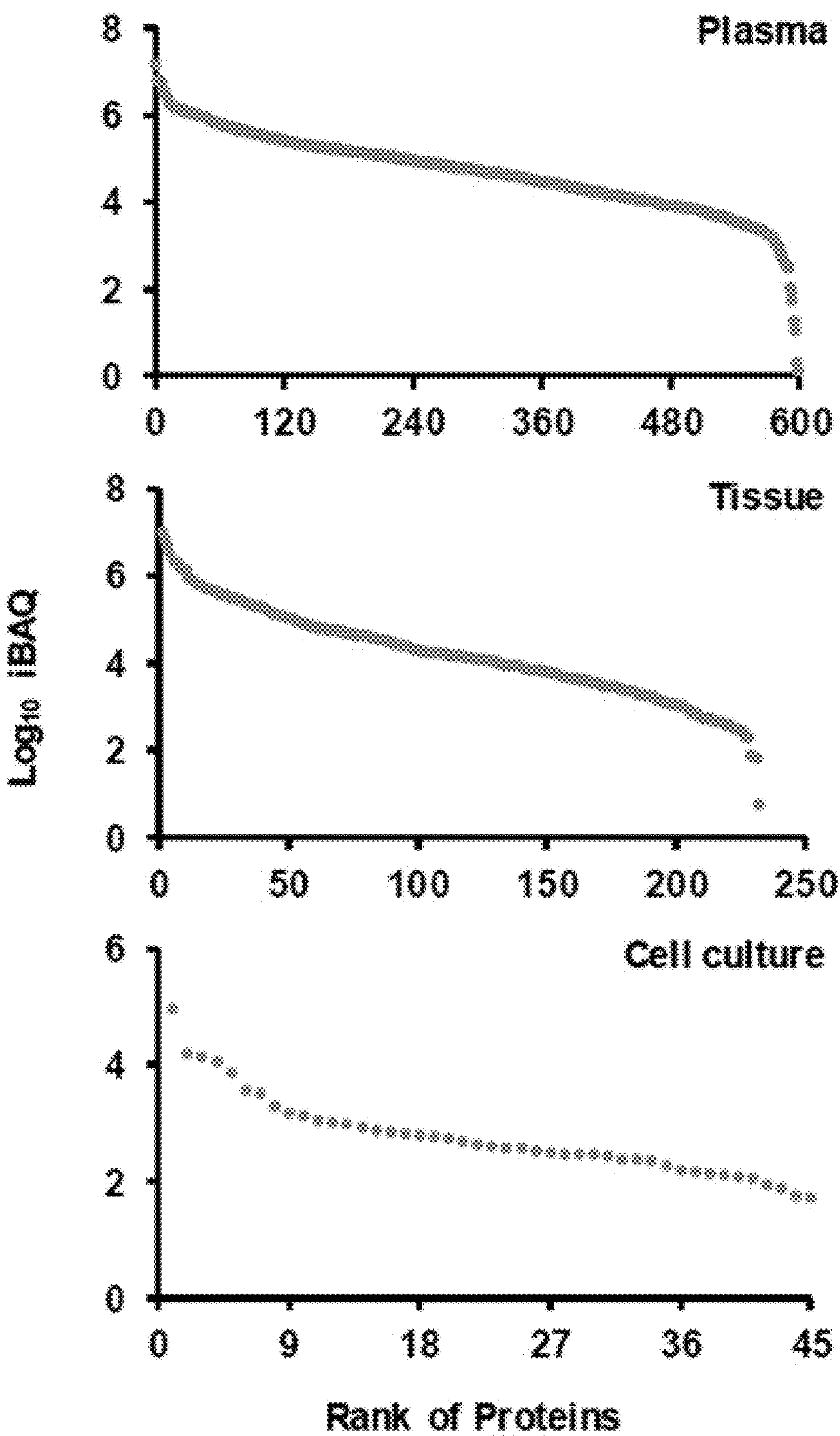

Human exosome-derived proteins from the different sources (plasma—yellow, top set; tissue—blue, middle set; and AsPC-1 cancer cells—red, bottom set) were subjected to gene enrichment analysis using FunRich 3.1.3 in which the proteins were categorized by GO Biological Process (FIG. 13B), GO Cellular Component (FIG. 13C, with top two sets referring to plasma, the middle set referring to tissue, and the bottom set referring to AsPC-1 cancer cells), and GO Molecular Function (FIG. 13D, plasma—yellow, top set; tissue—blue, middle set; and AsPC-1 cancer cells—red, bottom set). These categories represent the annotation of the functional enrichment of specific proteins, and the data are presented as the −log 10 (p-value) with a higher value representing greater functional enrichment of a category. The biological processes associated with the identified proteins independent of the source were: energy pathways, protein metabolism, and cell growth and/or maintenance. However, only the cell growth and/or maintenance were significant in all three sources (−log (p-value) in plasma=4.48, tissue=3.58 and ASPC-1 cancer cells=1.80, FIG. 13B). In the cellular component analysis, exosome, lysosome, and extracellular were the most highly represented categories from the isolated exosomes—independent of the source with p-values of <0.001. This analysis also revealed high proportions of proteins from the mitochondrion, cytoskeleton, or centrosome. The distribution of cellular components is shown in FIG. 13C. Specific molecular functions were overrepresented in the proteins identified from human exosomes isolated from plasma, tissue, or cell culture, and are likely related to the enriched biological process: energy pathways and/or protein metabolism, among which calcium ion binding, cell adhesion molecule activity, protease inhibitor activity, and structural constituent of cytoskeleton are notable because they are enriched in at least two out of three different sources of human exosomes analyzed (FIG. 13D). Finally, a genetic network was constructed using Cytoscape to ascertain information about protein-to-protein interaction of STRING db and the transcription factors that were enriched in the common proteins (FIG. 13E). This shows that FOS, FOSB, JUN, JUNB, and JUND regulate a shared number of proteins with high significance as well as BACH1, which all play important roles in cancer.

The iBAQ intensity of exosome proteins isolated from plasma, tissue, and ASPC-1 cells include 5.6, 5.2, and 3.2 orders of magnitude, respectively. Within this set of proteins, regardless of the source of exosomes, we found several tumor-related proteins including: TFRC, LDHA, B2M, CD44, CEACAM1, CEACAM6, EGFR, ENO2, FTH1, and MUC1 and proteins commonly used as exosome markers including: A2M, ACTG1, ALB, ANXA2, ATP1A1, BSG, GAPDH, PRDX1, and TPI1 according to Exocarta. Examination of individual proteins also revealed subtle differences in protein levels from diverse pancreatic cancer exosomes. An interesting subset of the proteins identified in plasma isolated-exosomes included: TSPAN1, IGKV4-1, TSPAN8, TMEM116, B2M, and TMEM14C. The tetraspanin, tetraspanin-enriched microdomains containing proteins, and proteins with immunoglobin domains play important roles in extracellular vesicle biogenesis, the selection of exosome cargos, the binding and uptake of exosomes by target cells, or the ability of exosomes to present antigen. Some functional implications could underlie the absence of substantial levels of these proteins in tissue-isolated exosomes. Finally, the presence of a transcription factor TFAP2D, a transcription factor of the family of activating protein-2 that play essential functions in cell growth, differentiation, and apoptosis, but has low expression levels in pancreas, was identified in the top two proteins in tissue exosomes and top 15 proteins in plasma exosomes.

A new approach and a standard operation protocol (SOP) was presented for the isolation of exosomes both from tissues tissue extracellular matrix, and small volumes of plasma samples. This is the first demonstration of a mechanical nano-filtration approach for the isolation of exosomes from tissue samples. The unique ability of an in-house developed platform allows for isolation and analyzation of tissue and plasma derived exosomes using a single method and integrating it with SOPs. A downstream proteomic analysis was also performed to compare the proteomic cargo of tissue and plasma derived exosomes, where overlapping proteins in circulation and in the cancerous tissues were identified in a pre-clinical model. Currently available exosome isolation methods are not compatible with multiple complex sample matrices, such as culture media, plasma, serum, urine, saliva or tissue samples. Utilizing one standardized method that can process various sample types with similar processing steps with standard operation protocols, enables-omics downstream analysis and comparison for biomarkers discovery for early detection and therapy monitoring in the future.

By leveraging this unique ability, it is shown that exosomes can be isolated from a humanized PDAC mouse model with high yield and purity. It takes advantage of the proteins that were unique to human sequences to remove contaminant background mouse protein and focus the analysis. A subset of human proteins were also identified, which are important in cancer, including carcinoembryonic antigens cell adhesion molecules (CEACAM1, CEACAM6) and mucins (MUC1, MUC13) in the plasma exosome samples. In addition, comparative proteomic analysis of cancer tissue-derived exosomes from plasma exosomes revealed differences in exosomal content including proteins involved in cell growth, energy metabolism, cell adhesion, and extracellular matrix remodeling. These demonstrate our ability to detect important cancer-related proteins from these samples. We also demonstrated overlapping exosomal proteins in cancer cell culture media, bloodstream and in the cancerous tissue in a pre-clinical cancer model. This suggests that while cancerous tissue is shedding cancer related exosomes into circulation, there is also a subpopulation of exosomes residing in the cancer microenvironment. We successfully correlated exosomal protein signatures isolated from in vitro cell cultures and in vivo samples; circulating in plasma and exosomes in the cancerous tissue. It is contemplated that subpopulations of exosomes in the plasma could be investigated to better understand the molecular information that reflects the tumor in the tumor-derived exosomes.

Recently, improved isolation techniques and downstream analysis has facilitated the exosome research. Utilizing antibodies generated against to the surface biomarkers of exosomes, such as tetraspanins, enables highly specific capture of exosomes. However, focusing on surface markers for exosome isolation is not only labor intensive and expensive, at the same time these systems represents only a small subset of exosomes, which are heterogeneous in nature, especially in cancer. The disclosed approach to use a size-based mechanical filtration method enables to work with a larger cohort of exosomes to investigate the potential disease-related markers. This kind of approach is suitable for mass spectrometry-guided proteomics analysis. The ExoTIC approach is low-cost, scalable, reproducible, and rapid technique that can be implemented on large numbers of low volume clinical samples. This technology platform and the insights developed in future pre-clinical and clinical studies can be broadly applicable in developing multiomics diagnostic platforms from plasma and other samples across various pathological conditions such as cancer, diabetes, and infectious diseases.

The various methods employed in this example are now detailed in the subsections below.

Methods: Fabrication of the ExoTIC Device

As we described previously (as is described in the above-referenced patent application publication), the ExoTIC device comprises a pair of axial plates between which ring-like gaskets are captured that secure a membrane, a low protein binding, track-etched polycarbonate filter membrane with a 50-nm pore size, and a polyethersulfone (PES) filter in place. The PES filter along with a supportive paper pad provides the structural support for the filter membrane during device operation. A flow chamber is collectively defined between the walls of the plates and gaskets. One of the axial plates has an inlet opening, while the other has an outlet opening. The inlet opening is connected to the flow chamber. All sample volume flowing from the inlet to the outlet passes through the membrane, filter, and supportive paper pad, respectively. To create a tight seal around the periphery, the plates are secured to one another by a ring of compressive fasteners (bolts and nuts) which encircle the circumference of flow chamber.

Methods: Generation of Orthotopic PDAC Mouse Model

The AsPC-1 cell line (human pancreatic carcinoma) was used to establish the orthotopic mouse model of human PDAC. In brief, AsPC-1 cells were propagated, in vitro. Following harvesting, tumor cells were injected subcutaneously into the flanks of five-week old female and male BALB/C (nu/nu) mice (n=6 per group) obtained from Charles River Laboratories. Once tumors reached 10 mm in size, animals were sacrificed. The tumors were explanted and were carefully dissected into small blocks of 4 mm, discarding any necrotic sections. Under general anesthesia, tumor recipient mice underwent into a midline surgical laparotomy under strict aseptic conditions. Following exposure of the pancreas, 3-5 micro-pockets were created in the pancreatic parenchyma into which donor tumor fragments were placed. The pancreas was then relocated back into the abdominal cavity.

Methods: Cell Culture for Exosome Isolation and Purification

AsPC-1 cells were cultured in DMEM (Life Technologies) supplemented with 10% fetal bovine serum (HyClone;

Perbio Sciences). Cells were cultured at 37° C. with 5% $CO_2$. For exosome isolation, cells were seeded in 75 $cm^2$ flask. Once the cells reached ~60-70% confluency, they were washed with PBS twice and incubated with DMEM media supplemented with 5% exosome-depleted FBS (Thermo Fisher Scientific) for 48 hours. After 48 hours, culture media was collected in 15 mL tube and centrifuged at 1,500 rpm for 10 minutes to pellet the cell debris. Supernatant was then passed through a 0.22 μm filter (Millipore). The resulting solution was processed through the ExoTIC device for exosome isolation, as described below.

Methods: Exosome Isolation from Cell Culture Media Using the ExoTIC Device

First, the ExoTIC device was flushed with PBS buffer using 10 mL syringe for 5 minutes. 10 mL of AsPC-1 cell culture media sample was processed through ExoTIC device with flow rate 5 mL/hour to extract exosomes. Then, the extracted exosomes were washed using PBS with ~20 times more volume than the concentrated exosomes, which was harvested by a simple withdrawing step using micropipette. Extracted exosomes were stored at −80° C. until further analysis.

Methods: Plasma Collection from PDAC Mice

PDAC mice were generated and maintained as described above. For terminal plasma collection, the mice were euthanized by $CO_2$ asphyxiation and were placed on their back (dorsal recumbence). The chest was wetted with 70% ethanol and the thoracic cavity was exposed by an incision through the ribs. Blood was collected with a 29 G syringe and dispensed into a microcuvette EDTA tube. Blood was mixed gently in the tube to ensure exposure to the EDTA-coated walls. Then, the plasma was isolated by centrifuging the blood sample at 2,000 g for 15 minutes at room temperature. The clear top layer was transferred to a labeled tube and stored at −80° C.

Methods: Exosome Isolation from Mouse Plasma Using the ExoTIC Device 50-100 μL of mouse blood plasma was diluted in PBS buffer at a 1:10 ratio. Diluted plasma sample was first filtered through 0.22 μm filter and then processed through ExoTIC device with flow rate of 5 mL/hour. Then, the extracted exosomes were washed using PBS with ~20 times more volume than the concentrated exosomes, which was harvested by a simple withdrawing step using micropipette. Isolated exosomes stored at −80° C. for further downstream analysis.

Methods: Exosome Isolation from Mouse Tissue Samples Using the ExoTIC Device

Orthotopic mice were sacrificed at 5-7 weeks of implantation and the primary pancreatic tumor were harvested as small pieces (~2 mm). Harvested tissue samples were stored at −80° C. until further use. For tissue digestion, 1 or 2 small pieces of pancreatic tumor tissue were treated with DNase-1 (Epicenter, 100 units/ml) overnight at 37° C. and were gently homogenized. Tissue homogenate was sequentially filtered through a 70 μm mesh filter and diluted with PBS to make the homogenate volume to ~10 mL. The diluted tissue homogenate was filtered with a 0.22 μm syringe filter. Filtered homogenate was then processed through the ExoTIC device at a flow rate of 1.5 mL/hour. Then, extracted exosomes were washed using PBS with ~20 times more volume than the concentrated exosomes, which was harvested by a simple withdrawing step using micropipette.

Methods: Nanoparticle Tracking Analysis

Nanosight (NTA 3.1 Build 3.1.46) was used to evaluate the size distribution and concentration of isolated exosomes. All the NTA results of the exosomes for each week were averaged and the mean size and error bars were reported based on the multiple read-outs.

Methods: Transmission Electron Microscopy of Exosomes

TEM analysis was performed based on a modified version of previously published protocols. See Thery, C.; Clayton, A.; Amigorena, S.; Raposo, G., Isolation and characterization of exosomes from cell culture supernatants and biological fluids. Current Protocols in Cell Biology 2006, 3.22.1-3.22.29. Carbon coated copper grids (Ted Pella Inc.) were glow discharged. All solutions were applied to the membrane-coated side of the grids. This side was kept wet for sample preparation steps, while the reverse side was kept dry. Isolated exosomes were mixed with an equal volume of 4% paraformaldehyde. Then, a 5 μL drop of the fixed exosome solution was placed on the TEM grid and allowed to incubate for 20 minutes while covered. Next, samples were washed and blocked by placing each one face down on top of 100 μL drops of the following solutions: PBS (2 times), PBS/50 mM glycine (4 times), PBS/5% BSA (one time). A 20 μg/ml solution of mouse anti-human CD63 antibody Clone TS63 (Abcam) was used for labeling (1 hour), followed by washes in PBS/0.5% BSA. Samples were incubated in a 1:50 dilution of goat anti-mouse immunogold conjugate (BBI) in 5% BSA/PBS and washed in PBS (6×) followed by water (6×). Finally, the samples were negatively stained with 1% uranyl acetate. Excess liquid was wicked away using Whatman No. 1 filter paper, leaving a thin film behind to dry. Imaging was performed in an FEI Tecnai TEM operated at 200 kV.

Methods: LC/MS Analysis of Exosomes

Tryptic peptide samples (5 μg) were loaded onto a PepMap 100 C18 trap column (Thermo Fisher Scientific) coupled to a Dionex Ultimate nanoLC (Thermo Fisher Scientific) in 0.1% formic acid in water at a 5 μl/min for 10 minutes. A C18 reversed-phase column (25 cm long Magic C18 AQ New Objective) was used to separate the tryptic peptides. Peptides were analyzed on a LTQ-Orbitrap Elite mass spectrometer (Thermo Fisher Scientific). The flow rate for separation was set to 0.6 μL/min. Mobile Phase A (0.1% formic acid in water) and Mobile Phase B (0.1% formic acid in acetonitrile) were set to 2% Mobile Phase B for the first 10 minutes and ramped up to 35% Mobile Phase B over 100 minutes, followed by a ramp to 85% Mobile Phase B over 7 minutes with holding for 5 minute additional minutes. Triplicate injections were performed for each sample. The ten most abundant ions in each MS1 scan were chosen for fragmentation higher energy collision induced dissociation (35 eV). Additional settings included: MS1 resolution=60,000, FT AGC target=1e6, and the m/z scan range=400-1800, MS2 AGC target=3e4, and dynamic exclusion=enabled for 30 seconds.

Methods: Data Analysis

Byonic 2.11.0 (Protein Metrics, San Carlos, CA) was used to search each data file twice: 1) using a Swiss-Prot database containing the reference human proteome (2017; 20,484 entries) and 2) using a Swiss-Prot the reference mouse proteome database (2017; 17,191 entries). The database search parameters were: trypsin digestion with ≤two missed cleavages, precursor mass tolerance<0.5 Da, fragment mass tolerance<10 ppm. Search parameters also included: fixed cysteine carbamidomethylation and variable methionine oxidation and asparagine deamination. A false discovery rate (FDR) filter of <1% was applied to peptide identifications. Peptides identified in both the human and mouse database searches were removed using an in-house R script to ensure human specific peptides. The area under the curve (AUC) of each identified peptide with two or more peptide spectral matches (PSMs) was extracted from the MS1 spectra to provide quantitative information using an in-house R script based on MSnbase package. Protein abundances were calculated as the sum of the AUC peptide intensities and divided by the number of theoretically identifiable peptides (calculated as the number of fully tryptic peptides by in silico digestion within m/z range between 400 and 1800 Th using dbtoolkit) according to the iBAQ algorithm. For the study of the biological functions of identified proteins, the proteins were categorized by GO Biological Process, GO Cellular Component, GO Molecular Function and those proteins that were commonly identified in two or more exosome sources were categorized according to the transcription factor that regulates it using FunRich 3.1.3.

Example IV: Isolation of Microvesicles

Extracellular vesicles (EVs) are one of the important parcels of the paracrine factors secreted by cells to the surrounding microenvironment that carry various bioactive cargos, i.e. genomic, proteomic and lipidomic cargo as well as organelles. These paracrine factors are unique, as they would provide a cell-free therapeutic strategy. Prior studies have been conducted using different animal models [2-6]. In this example, isolation of microvesicles (MVs) from culture media is shown and they contain active mitochondria or mitochondrial fragments.

Methods: MSC Culture

MSCs were thawed, washed once and resuspended in 10% FBS Dulbecco's Modified Eagle's Medium—high glucose (Sigma Aldrich), and plated in T75 flasks. Media was changed every 48 hours.

Methods: Microvesicle Isolation

Figure 21A:
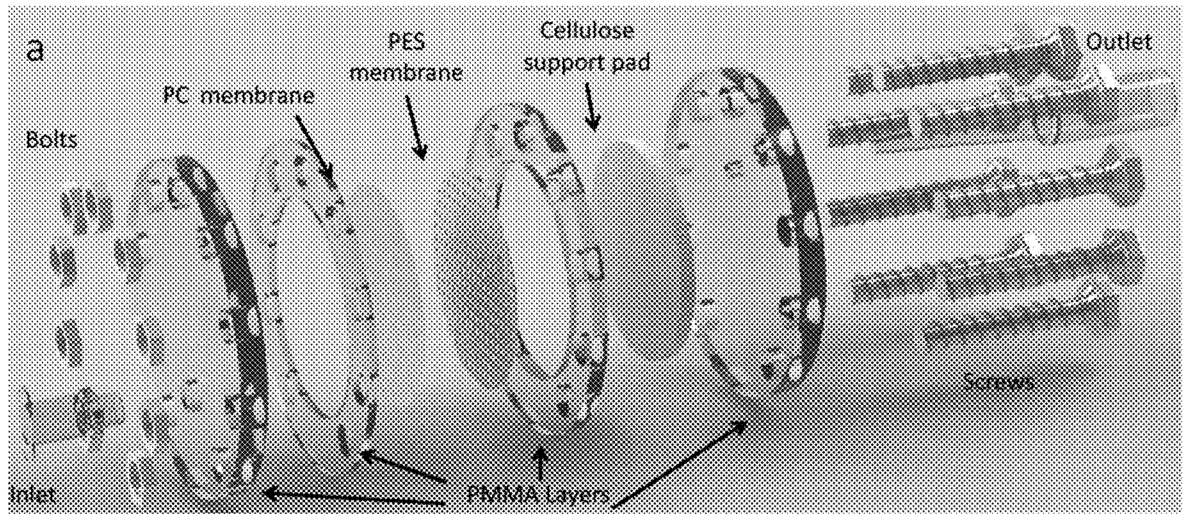
FIGS. 21A-C illustrates the Exosome Total Isolation Chip (ExoTIC) platform.
Figure 21B:
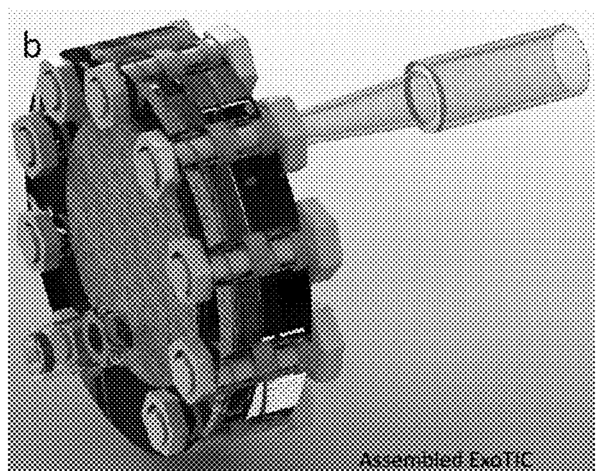
Figure 21C:
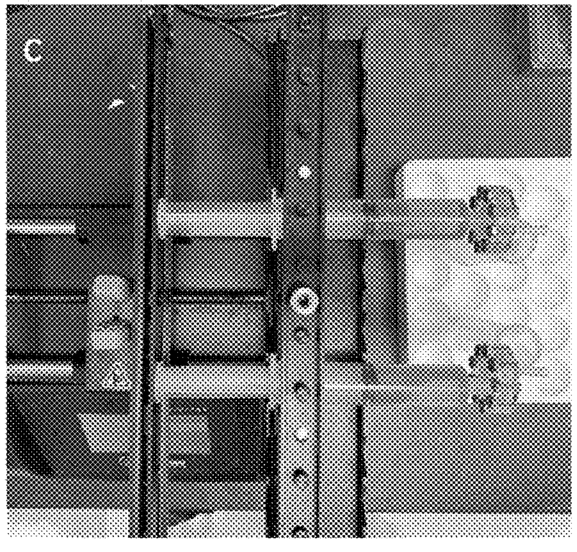
Figure 22A:
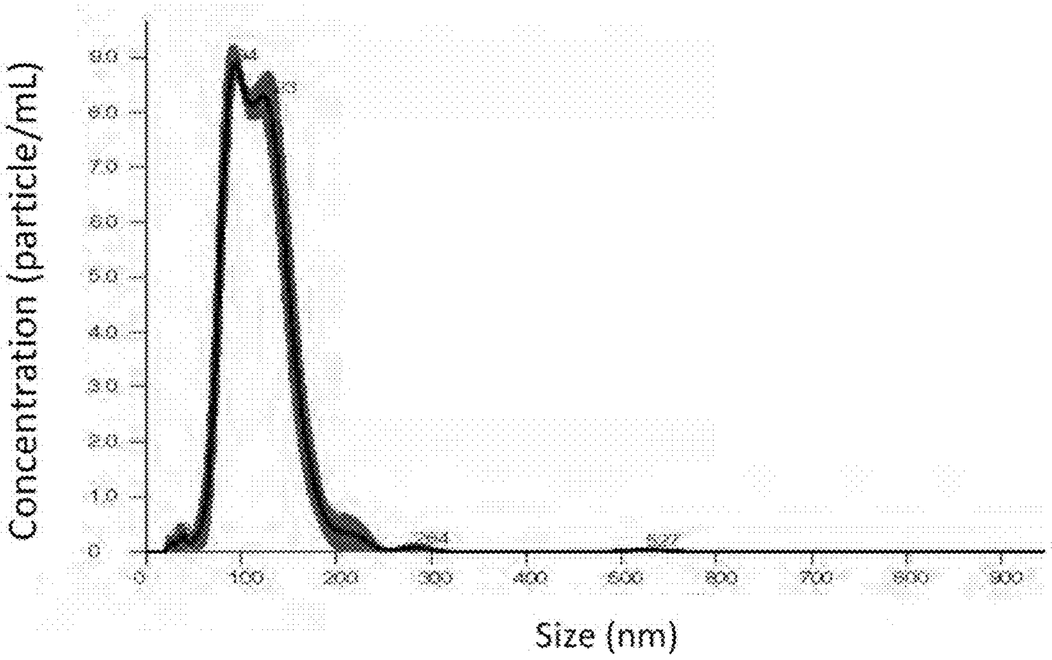
FIGS. 22A-B illustrate different extracellular vesicle subpopulations isolated by ExoTIC.
Figure 22B:
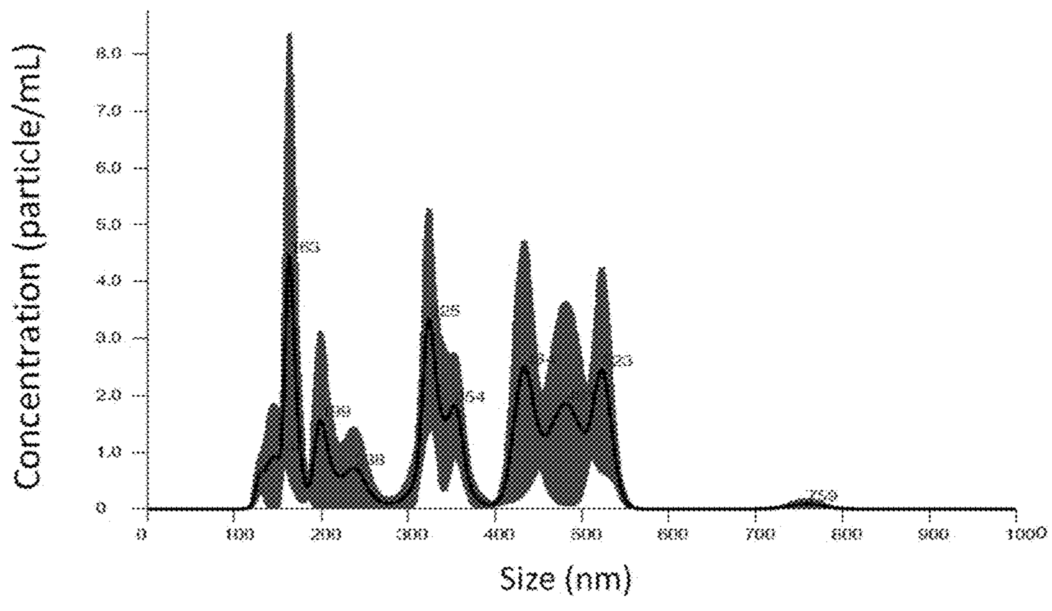

ExoTIC-MVs were isolated using a proprietary size-based filtration platform, Exosome Total Isolation Chip (ExoTIC, described elsewhere herein as well). ExoTIC was designed and built using inexpensive materials, such as filters, poly(methyl methacrylate) layers, nuts and screws (FIG. 21A-C). Supernatant was prepared by washing MSCs with PBS then adding Dulbecco's Modified Eagle's Medium—high glucose containing 10% exosome-free FBS (Systems Biosciences) to culture. After 48 hours of incubation MSC supernatant was collected and centrifuged at 500 g for 10 min at 4° C. Supernatant was collected for MV isolation. To isolate MVs, ExoTIC was decorated using a track-etched polycarbonate, low-protein binding filter with a pore size of 200 nm. Culture media sample was withdrawn to a syringe and mounted on a syringe pump. ExoTIC was assembled and preconditioned with PBS before attaching the chip to the syringe. In a 4° C. environment, a constant flow rate of 5 mL/h was applied to process the culture media to concentrate MVs in ExoTIC. Then, a new syringe filled with washing buffer (PBS for characterization studies and fresh culture media for functional studies) used to remove contaminating smaller vesicles allowing them to pass the filter in the same fashion as the culture media. ExoTIC-isolated MVs isolated in ExoTIC were harvested simply by a micropipette and used in further steps. NTA was performed to confirm particle size distribution and estimate concentration (FIGS. 22A-B). The solution containing microvesicles was stored at 4° C. and used immediately for experimentation.

Methods: Nanosight Analysis

MSC-derived exosome and microvesicle size and concentration were assessed by NanoSight (NS300, Malvern Instruments Ltd., UK). 1:50 dilutions of supernatant were prepared and analyzed in 60-second runs in triplicate. Camera level was determined by achieving particle concentration estimates of <5.106 and <1 particle per frame in DI water and unused culture media was used as a negative control. Video acquisition was performed under static, temperature-controlled conditions at 25° C. at Nanosight. Detection threshold was set to 5 during analysis.

Methods: TEM Imaging of Extracellular Vesicles

To validate the sizes of the extracellular vesicles isolated by ExoTIC, immunogold labeled TEM imaging was performed with negative staining. Briefly, a 10 μL aliquot of EV suspension harvested from ExoTIC and dropped on copper TEM grids with pure carbon support film. After the drop has dried, it was washed by a drop (~50 μL) of distilled water (3×) and the excess water was removed by using a filter paper. Afterwards, to reduce the nonspecific binding, the grid surface was blocked using 5% BSA solution (in PBS), and washed with 0.5% PBS (3×). Primary antibody solution (mouse anti-human CD9 IgG2B, Clone #209306, R&D Systems, MN, USA) diluted to 20 μg/mL using 1% BSA (in PBS) and incubated for 1 hour, followed by multiple dropwise washing steps with 0.5% BSA (in PBS) (5×). A secondary antibody conjugated with 10 nm AuNPs [goat anti-mouse IgG (H+L) (AH), 15751, TedPella, Inc., USA] was diluted 1:50 with 5% BSA (in PBS), applied dropwise to the grid and incubated for 30 minutes. The grid was then washed with first PBS (5×), then with DI water (5×). At the end, negative staining was applied using uranyl acetate (4%) with an incubation of 15 minutes and the excess liquid was removed by wicking with a filter paper from the edge of the grid. The imaging was then performed by FEI Tecnai TEM at 200 kV after the grids were dried at room temperature.

Results: Microvesicles (MVs)

Using a NanoSight NS3000 (Malvern Panalytical, UK) nanoparticle tracking analysis (NTA) showed a large distribution of EVs. The greatest population was always in the size range of exosomes (30-150 nm). In the representative NTA plot shown (FIG. 22A) the peak occurs at 108 nm and larger EVs range from 200 nm-850 nm. Based on this consistent particle size distribution, EVs were separated into exosomes and microvesicles (FIG. 22B).

Results: Transmission Electron Microscopy (TEM) Imaging of MVs

Figure 23:
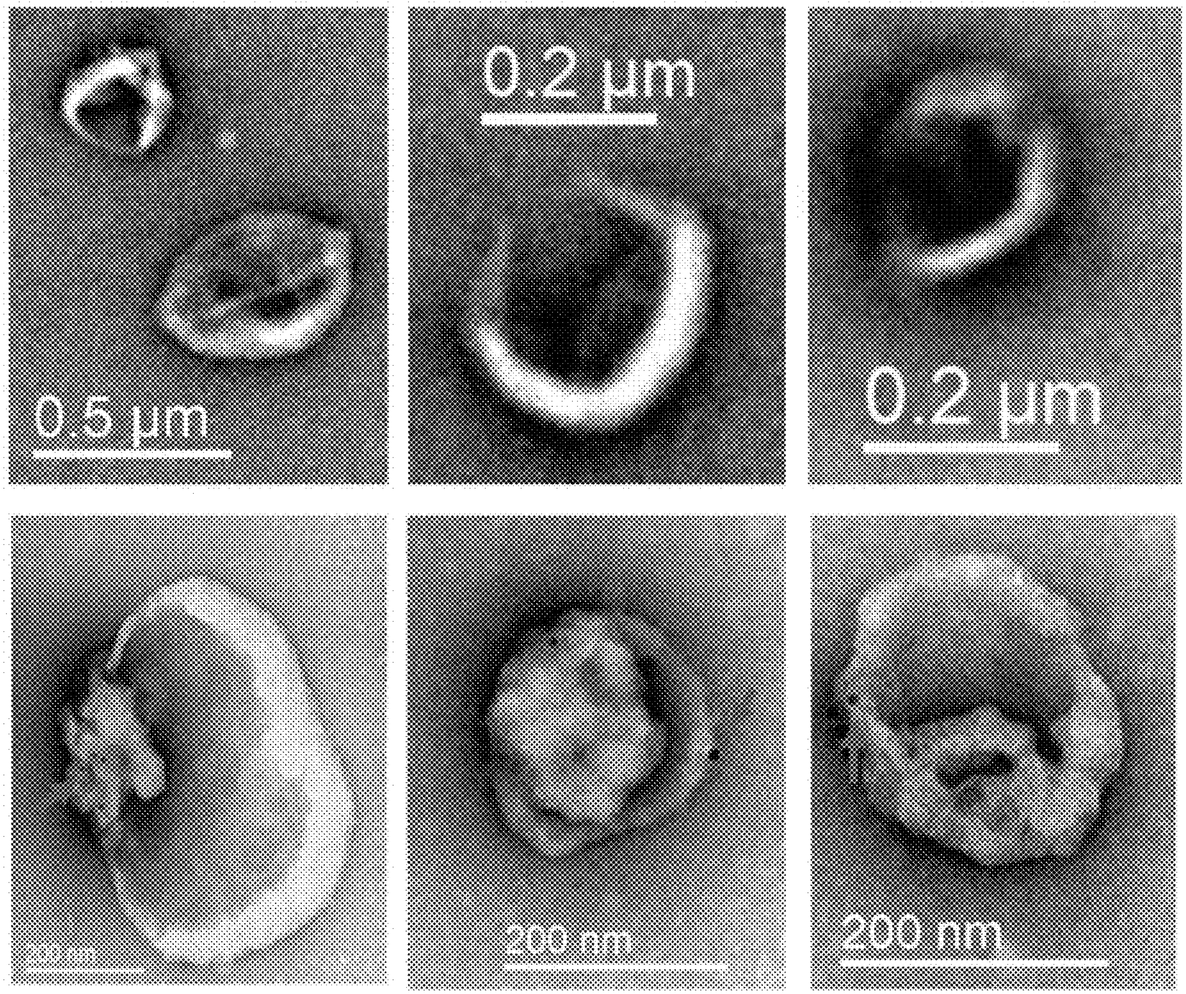
FIG. 23 illustrates ExoTIC isolated microvesicles imaged via TEM. Upper panel; negative staining of MVs with 250-500 nm diameter in size. Lower panel; immunogold (10 nm) labeling of MVs that are CD9+(arrows).

MVs were further characterized with transmission electron microscopy (TEM). TEM evaluation of MVs demonstrated a similar size range of MVs ranging from 220 nm-500 nm consistent with traditional MV size ranges (FIG. 23). Immunogold labeling using TEM showed our MSC-MVs to be CD9+(FIG. 23) further suggesting MV origin.

Discussion

Here, the ExoTIC tool is demonstrated to be capable of isolating MVs>200 nm that are secreted from MSCs. These vesicles can contain various cargo including; mitochondria or fragments, that can be used to improve mitochondria function, such as augmented ATP production, reduced ROS production, improved calcium flux and recovery, healing and stronger muscle cells contractility if used in cardiomyocytes.

Exosomes and MVs are two different types of EVs, lipid bi-layered membrane particles in various size and cargo content, have caught attention in biomarker identification, disease diagnosis, monitoring, prognosis, and therapy research in recent years. There have been different commercial and lab-based methods developed and used to isolate EVs using their intrinsic physical and biochemical properties. Heterogeneity in EV isolation technique renders interstudy comparison of EV-mediated results challenging since each isolation method has its intrinsic advantages and disadvantages. In this example, it is demonstrated that ExoTIC can serve as EV isolation platform that is easy-to-use, low-cost, highly efficient, batch-fabricable, and minimizes user-related errors. ExoTIC has a flexible design to isolate different subpopulations of EVs by utilizing different pore-sized filters, where this example focused on MVs.

Example V: Exosomal DNA (exoDNA) Enrichment Using ExoTIC

Liquid biopsy (LB) is sampling and further analysis of bodily fluids, i.e., blood, for diagnosis and monitoring of diseases, especially for cancer, without the burden of a surgical operation needed for a solid tissue biopsy sample. Genomic and proteomic assays evaluating LB samples can specifically detect mutations that are generated by abnormal proliferations in cancer. Especially, cell free DNA (cfDNA) has been an excitement in LB research as a newly emerging biomarker. LB also has various limitations, such as; (i) it detects mutations in advanced-stage disease in majority of cancer patients, (ii) diagnostic sensitivity might be low since patients with early cancers can have less than one mutation per mL of plasma, (iii) cannot identify origin of the mutation addressing the tumor location since same genes can drive multiple cancer types in the same individual, (iv) especially cfDNA is openly circulating in blood, subject to its microenvironmental conditions, therefore its isolation is burdensome and low in yield, requiring large volumes of blood samples discomforting for the cancer patients. Hence, new LB components might help with some of these challenges by adding more to the information.

Figure 24:
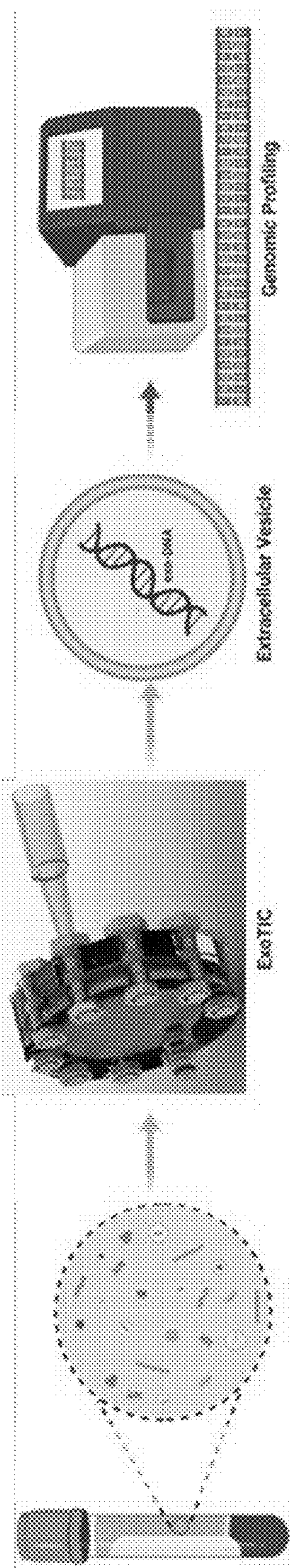
FIG. 24 is a schematic of DNA sequencing pipeline from with ExoTIC isolated EV-derived DNA.

EVs have emerged as exciting new LB components in the recent years as their cargo is preserved in an enclosed system with bi-layered lipid membrane protecting its heterogenous cargos, i.e., proteins, RNA, and DNA molecules, from degradational microenvironmental effects. One of the biggest challenges for establishing a well-defined EV-related LB pipeline for cancer diagnosis is the lack of a reliable isolation method, which is also still an unsolved problem for circulating tumor cell DNA and/or cfDNA isolation for further analysis. EVs have been reported to carry cancer related proteins, coding and noncoding RNAs that can be used as biomarkers, but the number of studies related to exoDNA have been limited due to this reason, leaving exoDNA as an underexplored component in liquid biopsy. Efficient isolation of exoDNA, investigation of its utility and side-by-side comparison to cfDNA has been both an appealing and challenging topic for further investigation (FIG. 24).

Rapid isolation and characterization of EVs is challenging, where ultracentrifugation is time and user-dependent, while PEG based methods are low in yield and loose significant portion of the smaller exosomes, which makes it harder to isolate exoDNA (Table 1, below). Due to these limitations, there is no method that can efficiently isolate exoDNA for further downstream analysis. Although surface markers elect subpopulations of exosomes, they do not necessarily predict the DNA or other cargo packed. Hence, no specific selection method exists for isolating exosomes for a specific cargo. Especially, DNA carrying exosomes are reported to be lower in concentration requiring either processing much larger volumes or higher yield methods. Given the patient samples from biobanks are precious and limited in quantity most of the time, the only solution is to develop methods that can yield higher isolation of EVs encapsulating DNA.

TABLE 1

EV isolation methods, working principles, advantages and disadvantages.

| Method | Principle | Advantage | Limitations |
|---|---|---|---|
| UC | Differential sedimentation based on particle density and size, can be combined with other methods for higher purity | Most frequently used method | Low yield Time Consuming Expensive User-to-user variation |
| Size exclusion | Serial filtration and chromatography | Inexpensive and easy- to-use | Lack of efficient concentrations of EVs Risk of breaking EVs down to smaller EVs |
| Immune affinity | Antibody-based Sensitive | High sensitivity and specificity Allows to isolate certain subset of EVs | Expensive Antibody cross-reactivity Low yield |
| Microfluidics | Microscale isolation in channels | Low input volume, Can be combined with affinity-based methods | Low yield Needs validation Can have complicated steps |
| Polymeric precipitation | Precipitation of exosomes or EVs in dissolved polymers | Fast and efficient Increased yield Can be combined with other methods | Can isolate all the particles Expensive |
| Porous structures | Trapping particles | Fast | Only suitable for small EVs Needs validation |
| ExoTIC | Trapping particles | Fast, easy-to-use, cheap, standardizable, Increased yield, portable, flexible | Duration but multiplexing minimizes the required time. |

This example presents that isolated exoDNA optimizing the ExoTIC for this purpose comparing exoDNA to cfDNA in patient plasma samples and demonstrates a unique capability with this method that can reliably and reproducibly isolate exosomes with DNA content. Here, it is shown that exoDNA is longer in size, can represent the whole genome including the cancer specific mutations in tumor fractions with 4 times less sample requirement.

Figure 25A:
FIGS. 25A-B illustrate EV isolated plasma samples from participants with cancer, #1 no treatment (FIG. 25A) and #2 after treatment (FIG. 25B).
Figure 25A:
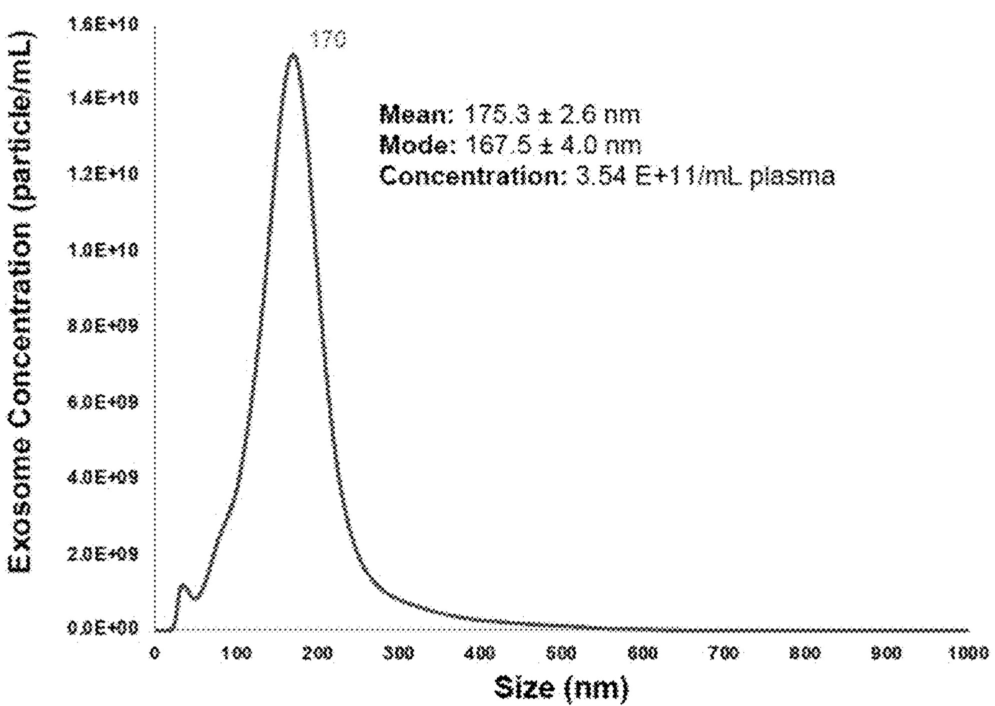
Figure 25B:
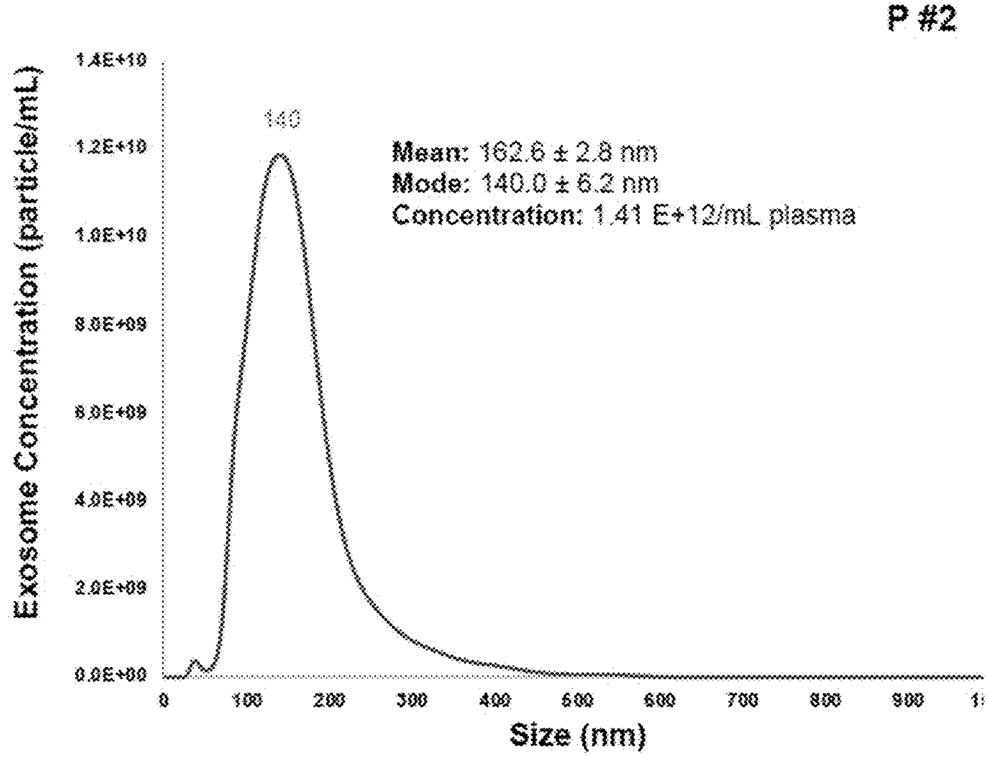

Again, an in-house developed EV isolation tool, Exosome Total Isolation Chip, ExoTIC, was utilized to isolate exosomes from plasma samples for downstream analysis (FIG. 24). ExoTIC leverages precise filters that houses nanometer size pores allowing us to isolate exosomes from plasma samples. It also differs from the other commercially available or instrument dependent methods available to the researchers by isolating the EVs as a size-based sorting platform. The washing step after the isolation step also helps to clean exosome preparations for a better downstream analysis. The developed platform has 1,000-fold increased EV isolation yield compared to ultracentrifugation, and ~3-fold increased isolation yield compared to polymer-based exosome isolation methods. Utilizing this advantage of ExoTIC, two participant plasma samples were processed where both participants have been diagnosed with cancer. Patient #1 has received drug therapy while patient #2 has not received any therapy for the disease. Patient #1 and #2 had a similar EV size distribution profile where patient #2 had ~4 times more EVs with mode peak diameter of 140.0±6.2 nm in size. On the other hand, patient #1 had bigger EVs in size, 167.5±4.0 nm. The total number of exosomes was $5.98\times10^{10}$ for patient #1 (FIG. 25A) and $7.5\times10^{10}$ for patient #2 (FIG. 25B).

Fourteen plasma samples from cancer patients and healthy individuals were processed. cfDNA and exoDNA were isolated and compared. For efficient cfDNA isolation minimum 3 mL plasma will be required to perform downstream analysis. However, for exoDNA isolation only 0.9 mL of plasma sample was used and obtained enough DNA for downstream analysis. By using less volume of plasma sample, similar quantities of DNA can be obtained for downstream analysis.

This example also reports a direction that exoDNA can represent cfDNA providing information about therapy response in cancer patient plasma. For further statistical investigation (t-test), prospective, randomized controlled trials including larger samples in order to make a more comprehensive analysis would be needed.

Methods: Sample Collection and EV Isolation

Plasma was separated using centrifugation the first at 2000 g for 20 minutes. Separated plasma was then stored at −80° C.~1 mL plasma samples of both participants were pre-filtered with a syringe type 0.22 μm filter to separate EVs from remaining cell and cell debris in the samples after being diluted 20 times using PBS. Then, samples were withdrawn into 10 mL syringes and mounted on a syringe pump with multiple channels. The samples were processed with a flow rate of 5 mL/hour, and washed PBS with new syringes as described earlier. After washing step, the concentrated EV solution was pipetted out from the ExoTIC and kept at 4° C. overnight with the membrane that isolated vesicles, to disassociate the trapped particles to the PBS solution. Then EV solutions were further concentrated with centrifugal evaporator at room temperature for 2 hours. After this step further concentrated EV preparations were frozen at −80° C. for further studies.

Methods: EV Quantification

ExoTIC isolated EVs were quantified using nanoparticle tracking analysis (NTA) using NanoSight™ (Malvern, UK). 20 μL of EV preparations were diluted with DI water and introduced to the device for analysis. Quantification results were given in FIGS. 25A-B.

Methods: Exo-DNA and Cf-DNA Isolation and Quantification

Exo-DNA was extracted using QIAmp DSP Mini Kit 50, version 2. Ed (Qiagen, Germany), where cfDNA was isolated from another aliquots of plasma from the same participants with Qiagen Min Elute kit (Qiagen, MD, US). Isolated DNA from both sample types were quantified and characterized using Qubit 3 fluorometer with high sensitivity dsDNA assay (Thermo Fisher Scientific).

Example VI: Isolation EVs from Plasma Samples of HIV Patients with Different Viral Load One of the primary challenges in the development of therapeutic or curative therapies for viral diseases is the identification and characterization of biomarkers or signatures of acute, latent or persistent infection that have diagnostic, prognostic or therapeutic potential. The overall goal of this example is to implement a technologically innovative pipeline to discover and characterize such markers through circulating Exosomes. Methods are developed, validated and implemented using HIV persistence as a model system, which will provide the experiences to rapidly adapt the "pipeline" to other established or emerging infectious diseases of global concern.

Despite the ability of combination antiretroviral therapy (ART) to reduce HIV-related morbidity and mortality, viral reservoirs persist in latently infected cells for which there are no effective ways to identify or characterize. These infected cells may persist in less than 1 in 1,000,000 circulating lymphocytes, and the bulk of the HIV reservoir exists in tissues that are difficult to sample. Circulating biomarkers are urgently needed that can assess the size and activity of persistent infection or to demonstrate efficacy of various viral eradication strategies. Discovery of such markers will also facilitate development of novel, specific therapeutic targets to eliminate or control infection.

Exosomes are nanovesicles up to 120 nm in diameter that are secreted into the extracellular space, as well as a wide variety of body fluids (e.g., plasma, urine, cerebral spinal fluid, semen, and breast milk). Exosomes are relatively stable in circulating fluids, and can be internalized by recipient cells leading to modulation of various signaling pathways and physiological processes. Exosomes may contain functional mRNA and microRNAs (miRNAs) in addition to a larger variety of protein and lipid cargos, and are now recognized as important for mediating pathophysiologic responses to infections such as HIV. Exosomes also have the potential to provide important information about body-wide infectious processes in vivo, as exosomes can be released into blood from difficult-to-sample tissues and then analyzed. Therefore, it is proposed to perform in depth nucleic acid and protein characterization of exosomes to identify unique signatures or novel markers of persistent, latent infection, and eventually, other infections. Given the rarity and large diversity of HIV-infected cells in the setting of ART that may persist in a variety of unique tissue and immune environments, techniques are incorporated to detect single-exosomes signatures using high dimensional analyses that may be missed or diluted with bulk analysis alone. However, various challenges persist in the isolation and characterization of exosomes in the setting of infectious diseases. In this example, the ExoTIC platform is used to overcome these isolation and purification challenges and to improve nucleic acid and proteomic characterizations.

Methods

To validate the EV isolation repeatability of the developed ExoTIC platform, three healthy whole blood samples drawn into $K_2$EDTA tubes from Stanford Blood Center (~6 mL each) were obtained. Whole blood samples were pooled, and plasma was extracted by centrifuging the samples at 2000 g for 15 minutes at 4° C. Cleared plasma was obtained and aliquoted (100 μL of nine samples, the remaining plasma was frozen).

Figure 26A:
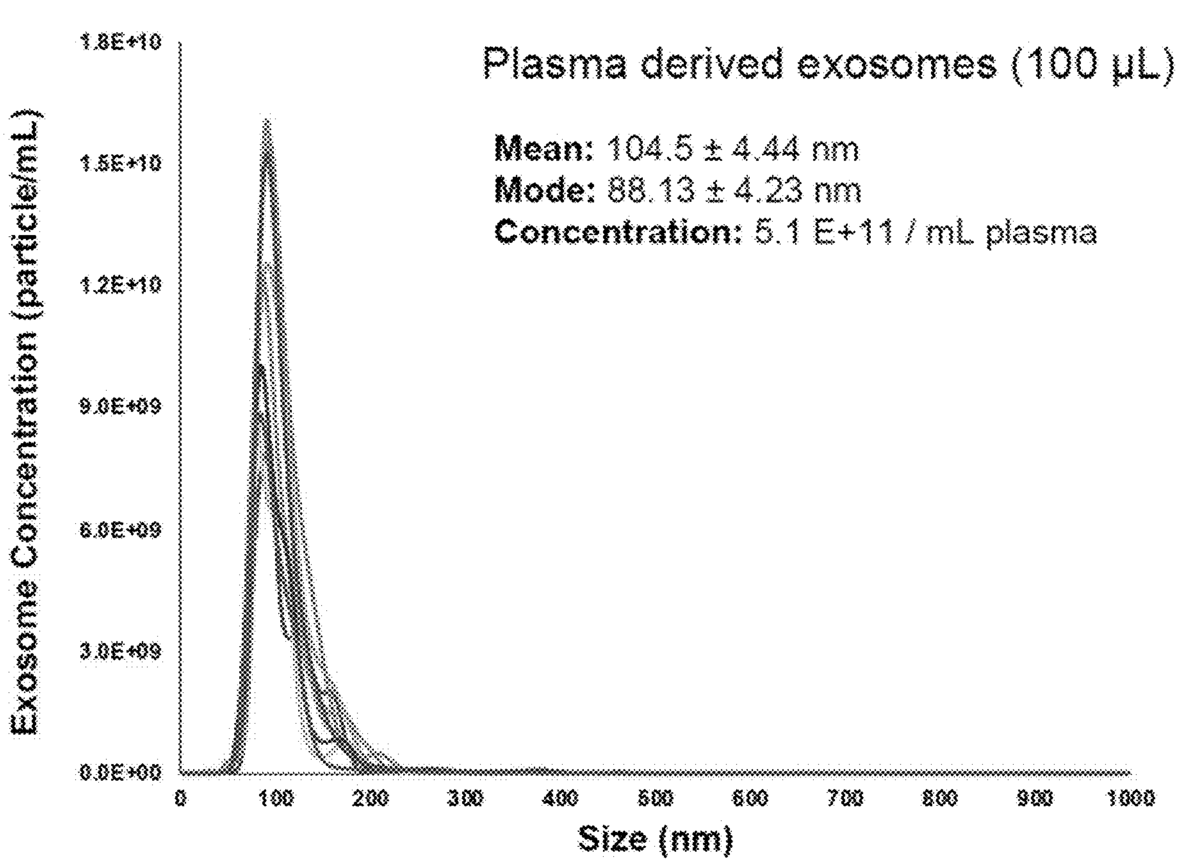
Figure 26B:
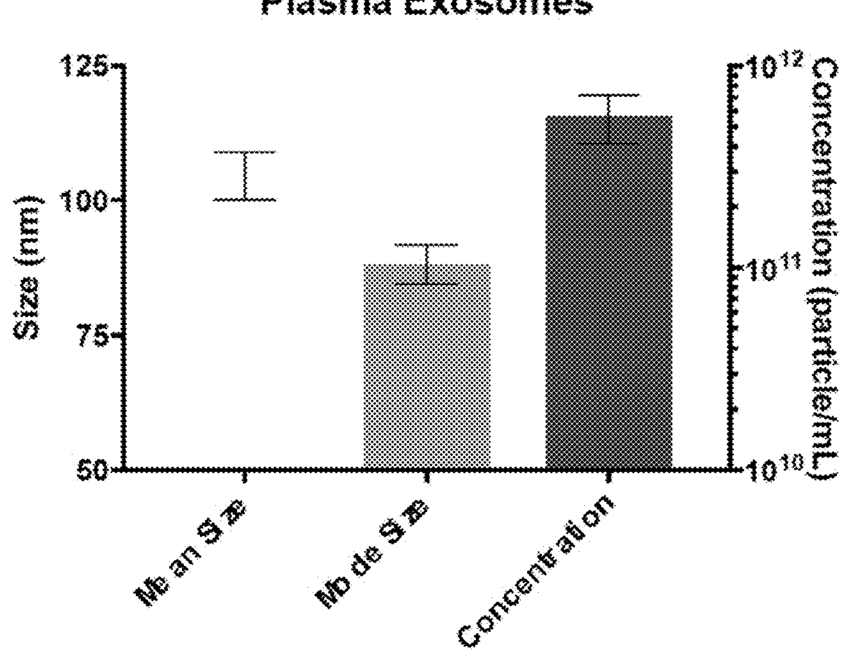

100 μL plasma aliquots were diluted with PBS (10 mL), filtered through a syringe type filter (0.22 μm) and withdrawn into a syringe to process via ExoTIC. Isolated EVs were analyzed using Nanoparticle tracking analysis for size profiling and quantification (FIGS. 26A and 26B). These results showed the rigor and repeatability of ExoTIC while processing plasma samples and the isolated RNA from these EVs were sufficient for RNA sequencing (FIG. 26C).

Ten HIV infected patient plasma samples with various viral loads with/without antiretroviral therapy were processed to isolate EVs and extract RNA for sequencing to identify novel miRNAs related with the HIV viral load and therapy outcomes (Table 2, below).

TABLE 2

The viral load, exosomal RNA extracted from EVs and their small non-coding microRNA (miRNA) concentrations of the samples.

| # | Viral Load (copies/mL) | Exosomal Small RNA (pg/μL) | miRNA (pg/μL) | miRNA/ Small RNA Ratio (%) |
|---|---|---|---|---|
| 1 | 0 < 20 | 175.8 | 82.4 | 47 |
| 2 | 0 < 20 | 174.5 | 61.7 | 35 |
| 3 | 0 < 20 | 234.5 | 118.0 | 50 |
| 4 | 31.5 | 126.5 | 60.5 | 48 |
| 5 | 384 | 42.9 | 33.6 | 78 |
| 6 | 39800 | 97.7 | 56.2 | 58 |
| 7 | 96900 | 105.5 | 54.4 | 52 |
| 8 | 23500 | 351.0 | 158.9 | 45 |
| 9 | 47300 | 223.9 | 92.2 | 41 |
| 10 | 50.8 | 349.9 | 130.4 | 37 |

In the next phase of the example, the plasma volume was studied as a parameter yielding the extracted RNA from plasma-derived exosomes. 100 μL and 500 μL of plasma samples obtained from healthy individuals from Stanford Blood Center were compared. A further concentration step to the procedure was implemented for further concentrating the isolated exosome sample using a vacuum centrifuge for 2 hours at room temperature. This added step further increased the extracted RNA concentration from samples by increasing the yield ~20× from ~50 pg/μL to ~1000 pg/μL as given in FIGS. 27A and 27B. Following this, total quantity of extracted RNA was 100 μL of plasma samples was increased from ~5 ng to ~30 ng. Also, RNA quantity was found to be ~45 ng when 500 μL plasma sample was utilized for exosome extraction.

Example VII: Exosomes from Platelets for Cosmetic Applications Similar to PRP Therapy All the cells in body produces exosomes. Exosomes are one of the smallest forms of cellular therapy available, because their function is to direct tissue formation, restructuring and wound healing by activating the patient's own regenerative cell response.

Stem cells and stem cell therapies target to be effective through paracrine signaling where cells affect other cells via the molecules, exosomes in our case, where they secrete to the shared extracellular space to build a healing environment to restore tissue components. Exosomes can be identified as the paracrine signals secreted from stem cells that can be delivered without presence of stem cells.

Besides stem cells, platelets, one the cells in the circulation clot takes significant role in blood clotting via cytokines and vesicles they secrete to initiate the healing processes. The platelet derived exosomes shown to be effective as therapeutic components of the blood by, promoting neural growth after crossing blood brain barrier, a PRP-derived exosome treatment can improve the re-epithelization of chronic cutaneous wounds via activation of YAP in a diabetic rat model, promote cardiac recovery after myocardial infarction, promote neutrophil-endothelial cell interactions in inflammation, mediate hyperglycemia-induced retinal endothelial injury via targeting the TLR4 signaling pathway, inhibits coronary vascular endothelial cell inflammation, alleviate knee osteoarthritis by promoting proliferation and inhibiting apoptosis of chondrocyte via Wnt/β-catenin signaling pathway.

These unique properties of exosomes make them potential candidates for cell-free therapies in facial and skin rejuvenation as anti-aging therapeutics, in wound healing after burns, in hair loss rejuvenation, and sexual wellness.

Example VIII: Preparation of Extracellular Vesicle-Depleted Samples for Downstream Analysis The extracellular vesicles (EVs) can be isolated as mentioned above. The EV-depleted samples can be collected at the outlet of the device, including smaller vesicles (30 nm<).

These smaller structures can be collected by a follow up device.

EV-depleted sample can be analyzed for non-extracellular vesicular profiling, including soluble proteins, metabolomics.

By depleting extracellular vesicles, EV-derived DNA can be compared to cell-free DNA, and EV-derived RNA can be compared to cell-free RNA.

It should be appreciated that various other modifications and variations to the preferred embodiments can be made within the spirit and scope of the invention. Therefore, the invention should not be limited to the described embodiments. To ascertain the full scope of the invention, the following claims should be referenced.

What is claimed is:

1. A method of processing an extracellular vesicle-containing sample using a device for extracellular vesicle isolation and isolating one or more subpopulations of the extracellular vesicles, the method comprising:

flowing the extracellular vesicle-containing sample through a flow chamber of the device for extracellular vesicle isolation under an applied fluid pressure, the device having inlets and at least two outlets which are placed in fluid communication with one another via the flow chamber, the device further having one or more filters in the flow chamber between at least one of the inlets and at least one of the at least two outlets, in which the inlets include different inlets including (i) at least one inlet for introducing the extracellular vesicle-containing sample to the flow chamber for flow through the one or more filters and (ii) at least one inlet for providing an evacuating flow to flow at least one of the subpopulations of the extracellular vesicles from a portion of the flow chamber, and wherein the at least one inlet for providing the evacuating flow is positioned between two filters of the one or more filters in the flow chamber such that the evacuating flow isolates the extracellular vesicles in the extracellular vesicle-containing sample having sizes between the two filter filtering sizes associated with the two filters and causes the extracellular vesicles that have been isolated to flow out a corresponding outlet of the at least two outlets;

during the step of flowing, flowing the extracellular vesicle-containing sample through the one or more filters in the flow chamber to sort the extracellular vesicles of extracellular vesicle-containing sample by size into two or more subpopulations of the extracellular vesicles; and using the evacuating flow, flowing at least one of the subpopulations of the extracellular vesicles that have been sorted by size after passing through the one or more filters out of a corresponding one of the outlets.

2. The method of claim 1, further comprising:

after the step of flowing the extracellular vesicle-containing sample through the one or more filters in the flow chamber to sort the extracellular vesicles of extracellular vesicle-containing sample by size into two or more subpopulations of the extracellular vesicles, introducing labeled magnetically-responsive particles to at least one of the subpopulations of the extracellular vesicles that are labeled to bind to at least some members of the subpopulations of the extracellular vesicles; and flowing the subpopulations of the extracellular vesicles through a channel having a magnetic field applied thereto to further separate members of the subpopulation that are bound to the labeled magnetically-responsive particles from members of the subpopulation that are not bound to the labeled magnetically-responsive particles and flowing those further separated members from different outlets of the channel.

3. The method of claim 2, further comprising, during introducing labeled magnetically-responsive particles to at least one of the subpopulations of the extracellular vesicles that are labeled to bind to at least some members of the subpopulations of the extracellular vesicles, acoustic mixing the magnetically-responsive particles with the at least one of the subpopulations of the extracellular vesicles.

4. The method of claim 2, wherein a combination of separation by mechanical filtration and binding to labeled magnetically-responsive particles of the at least one of the subpopulations of the extracellular vesicles fractionalizes extracellular vesicles by both size and surface markers.

5. The method of claim 1, wherein the at least two outlets include (i) at least one waste outlet for a portion of the extracellular vesicle-containing sample that has passed through all of the one or more filters and (ii) at least one filtered extracellular vesicle outlet out of which flows at least one of the subpopulations of the extracellular vesicles that have been sorted by size after passing through some, but not all, of the one or more filters.

6. The method of claim 1, wherein the at least two outlets includes: (i) at least one waste outlet for a portion of the extracellular vesicle-containing sample that has passed through all of the one or more filters and (ii) at least one filtered extracellular vesicle outlet out of which flows at least one of the subpopulations of the extracellular vesicles that have been sorted by size after passing through some, but not all, of the one or more filters.

7. The method of claim 6, wherein the at least two outlets include three or more outlets including at least one waste outlet for a portion of the extracellular vesicle-containing sample that has passed through all of the one or more filters and at least two filtered extracellular vesicle outlets out of each of which flow a corresponding one of the subpopulations of the extracellular vesicles that have been sorted by size after passing through some, but not all, of the one or more filters.

8. The method of claim 7, where the at least two filtered extracellular vesicle outlets sort the extracellular vesicle-containing sample into subpopulations of the extracellular vesicles having different and non-overlapping size ranges.

9. The method of claim 6, wherein in series, a filtration size of the one or more filters in the flow chamber progressively decreases between the at least one inlet for introducing the extracellular vesicle-containing sample and the at least one waste outlet for a portion of the extracellular vesicle-containing sample that has passed through all of the one or more filters.

10. The method of claim 9, wherein the filtration size of the one or more filters in the flow chamber are filters between 200 nanometers and 30 nanometers in size.

11. The method of claim 1, wherein the extracellular vesicle-containing sample includes exosomes released from pancreatic tumor tissue.

12. The method of claim 1, wherein the extracellular vesicles in the extracellular vesicle-containing sample are between 50-200 nanometers in size.

13. The method of claim 1, wherein, prior to the step of flowing the extracellular vesicle-containing sample through a flow chamber of the device for extracellular vesicle isolation under an applied fluid pressure, the extracellular vesicle-containing sample is pre-filtered to remove cells, bacterial contaminants, and other large cellular fragments.

14. The method of claim 1, wherein the extracellular vesicle-containing sample is or is derived from one of blood, plasma, urine, cerebral spinal fluid, semen, and breast milk.

15. The method of claim 1, wherein the one or more filters are nanoporous.

16. The method of claim 1, further comprising, before applying the evacuating flow, isolating a respective subpopulation of the extracellular vesicles between adjacent filters in which the respective subpopulation of the extracellular vesicles has a size distribution defined by a filtration range between the adjacent filters.

* * * * *